US010782511B2

(12) United States Patent
Igarashi

(10) Patent No.: US 10,782,511 B2
(45) Date of Patent: Sep. 22, 2020

(54) OBJECTIVE OPTICAL SYSTEM, ENDOSCOPE, AND ENDOSCOPE SYSTEM

(71) Applicant: OLYMPUS CORPORATION, Hachioji-shi, Tokyo (JP)

(72) Inventor: Tsutomu Igarashi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/665,325

(22) Filed: Oct. 28, 2019

(65) Prior Publication Data

US 2020/0064600 A1 Feb. 27, 2020

Related U.S. Application Data

(63) Continuation of application No. PCT/JP2018/009232, filed on Mar. 9, 2018.

(30) Foreign Application Priority Data

Jun. 2, 2017 (JP) .................................. 2017-110422

(51) Int. Cl.
*G02B 13/18* (2006.01)
*A61B 1/00* (2006.01)
(Continued)

(52) U.S. Cl.
CPC .......... *G02B 13/18* (2013.01); *A61B 1/00009* (2013.01); *A61B 1/00188* (2013.01);
(Continued)

(58) Field of Classification Search
CPC ........................... G02B 13/18; A61B 1/00013
(Continued)

(56) References Cited

U.S. PATENT DOCUMENTS

| 5,619,380 A | 4/1997 | Ogasawara et al. |
| 7,738,180 B2 | 6/2010 | Igarashi |

(Continued)

FOREIGN PATENT DOCUMENTS

| JP | H05341185 A | 12/1993 |
| JP | H07318799 A | 12/1995 |

(Continued)

OTHER PUBLICATIONS

International Preliminary Report on Patentability (IPRP) dated Dec. 12, 2019 (and English translation thereof), issued in International Application No. PCT/JP2018/009232.
(Continued)

*Primary Examiner* — Jeffery A Williams
(74) *Attorney, Agent, or Firm* — Holtz, Holtz & Volek PC

(57) ABSTRACT

An objective optical system includes in order from an object side to an image side, a first lens having a negative refractive power, an aperture stop, and a second lens having a positive refractive power. An image-side surface of the first lens is a surface which is concave toward the image side, and an image-side surface of the second lens is a surface which is convex toward the image side, and following conditional expressions (1), (2), (3), (4), (5), (6), and (7) are satisfied:

$0.6 < LL1is/LsL2i < 1.25$  (1)

$-3 < (LL1is/RL1i) \times (LsL2i/RL2i) < -1.25$  (2)

$-2 < fL2^2/(f \times fL1) < -1.35$  (3)

$2 < (nd1 - 1.63) \times (vd1 - 31)$  (4)

$5 < (n2 - 1.45) \times (vd2 - 31)$  (5)

$1.63 < nd1$, and, $31 < vd1$  (6)

$1.45 < nd2$, and, $31 < vd2$  (7).

18 Claims, 13 Drawing Sheets

(51) Int. Cl.
*A61B 1/05* (2006.01)
*H04N 5/225* (2006.01)
*H04N 5/232* (2006.01)

(52) U.S. Cl.
CPC ............. *A61B 1/05* (2013.01); *H04N 5/2254* (2013.01); *H04N 5/23229* (2013.01)

(58) Field of Classification Search
USPC .......................................................... 348/71
See application file for complete search history.

(56) References Cited

U.S. PATENT DOCUMENTS

| | | |
|---|---|---|
| 2009/0296235 A1 | 12/2009 | Igarashi |
| 2017/0123191 A1 | 5/2017 | Wang et al. |
| 2018/0017777 A1* | 1/2018 | Takasugi ............ A61B 1/00096 |
| 2018/0231763 A1 | 8/2018 | Ozao |

FOREIGN PATENT DOCUMENTS

| | | |
|---|---|---|
| JP | 2009288682 A | 12/2009 |
| WO | 2015122261 A1 | 8/2015 |
| WO | 2017090342 A1 | 6/2017 |

OTHER PUBLICATIONS

International Search Report (ISR) dated Jun. 12, 2018 (and English translation thereof) issued in International Application No. PCT/JP2018/009232.

Written Opinion of the International Searching Authority dated Jun. 12, 2018 issued in International Application No. PCT/JP2018/009232.

* cited by examiner

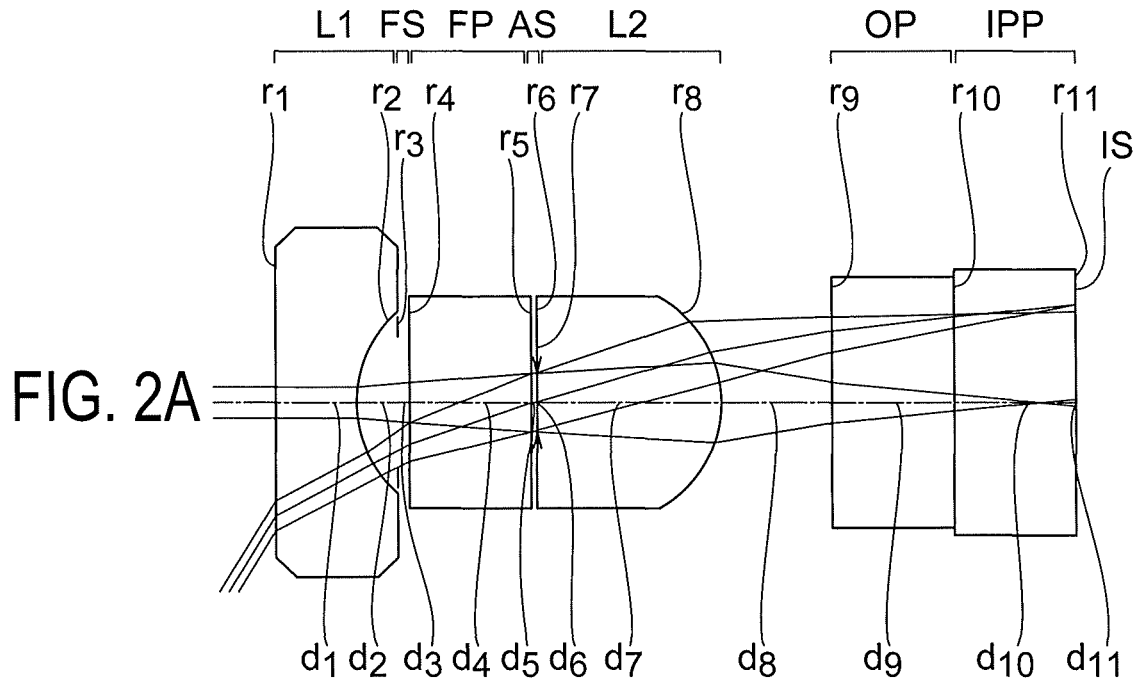
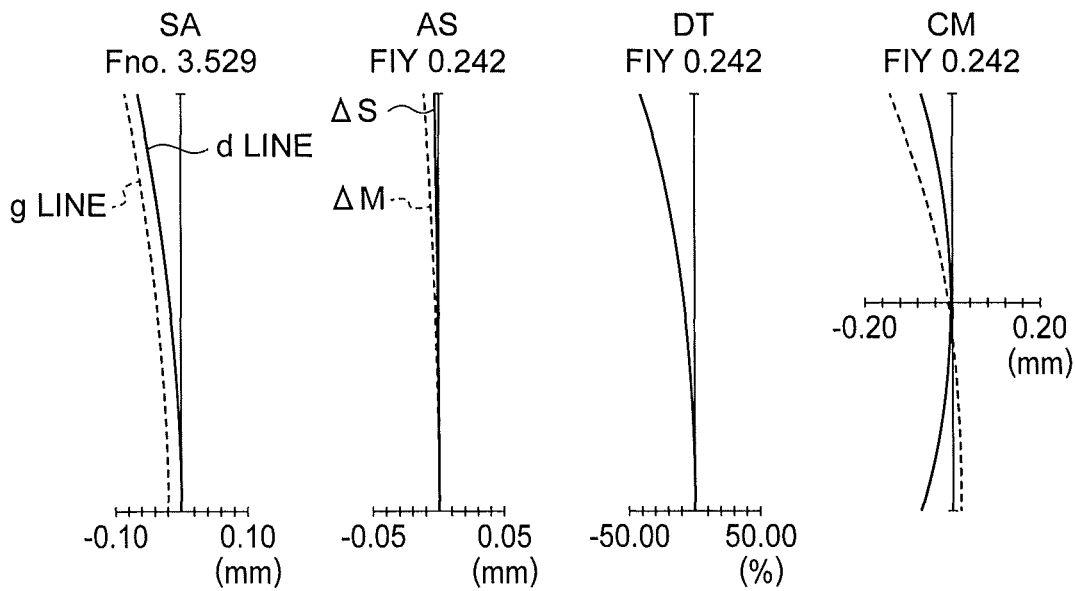

SA
Fno. 3.529

AS
FIY 0.242

DT
FIY 0.242

CM
FIY 0.242

SA
Fno. 3.514

AS
FIY 0.242

DT
FIY 0.242

CM
FIY 0.242

SA
Fno. 3.529

AS
FIY 0.242

DT
FIY 0.242

CM
FIY 0.242

SA
Fno. 3.508

AS
FIY 0.242

DT
FIY 0.242

CM
FIY 0.242

SA
Fno. 3.511

AS
FIY 0.242

DT
FIY 0.242

CM
FIY 0.242

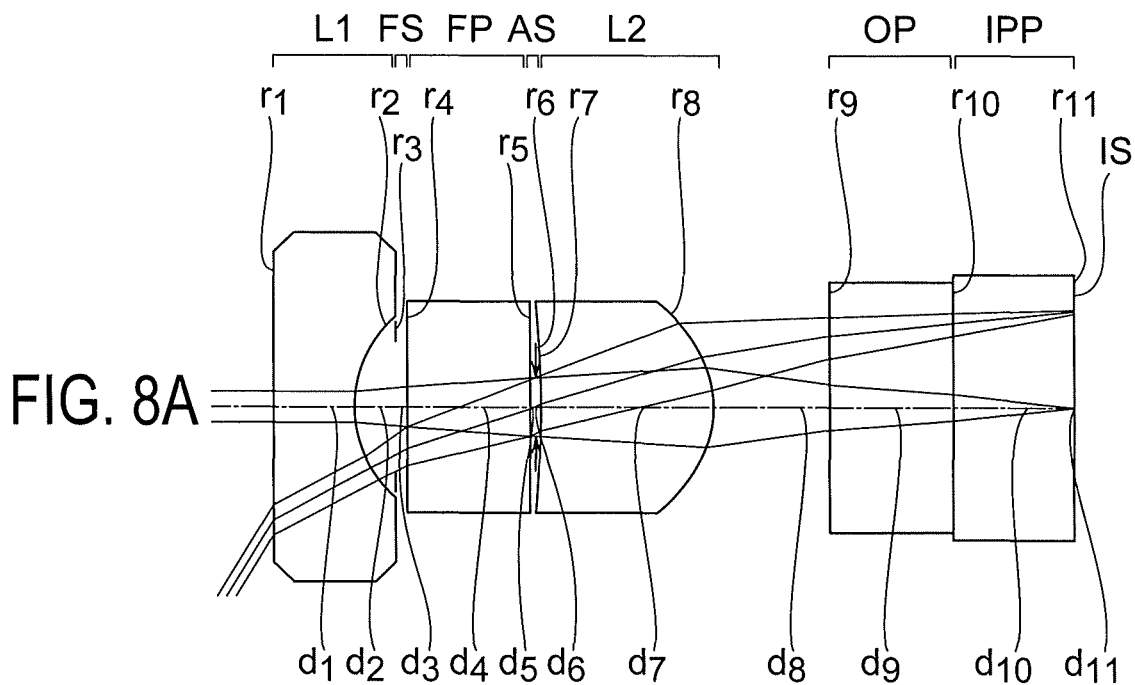
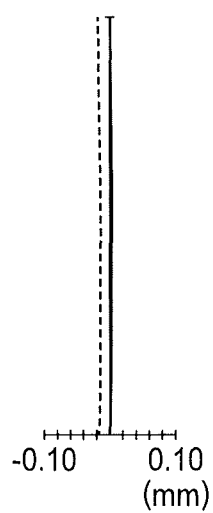 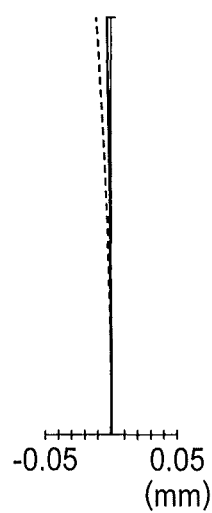 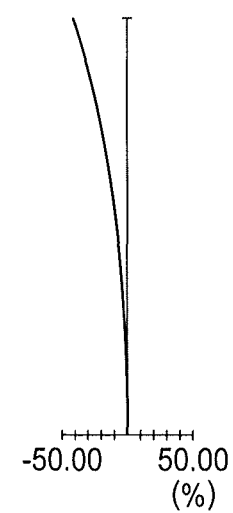 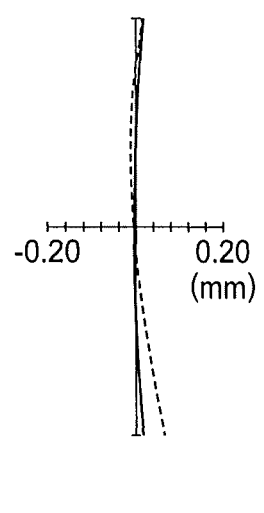

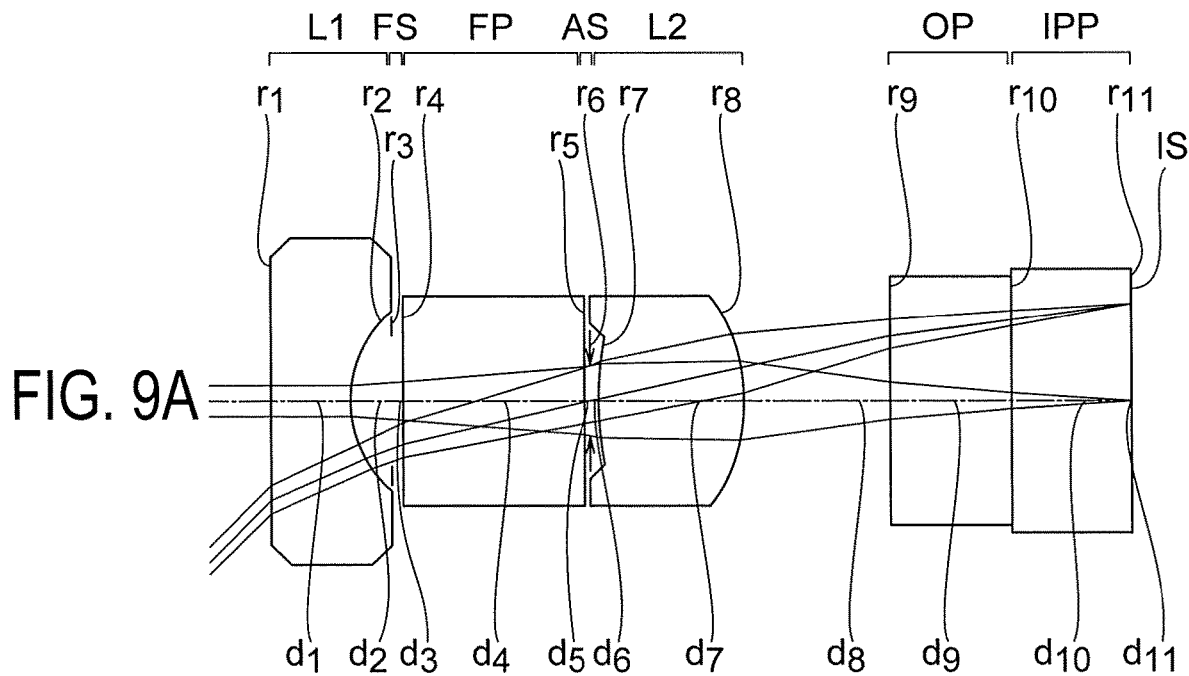
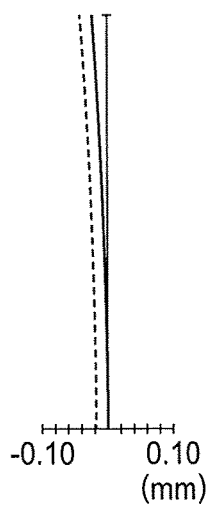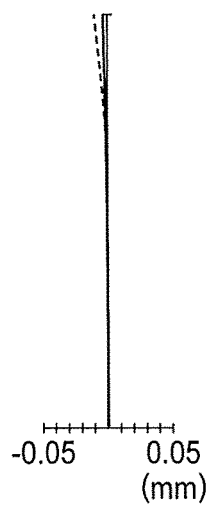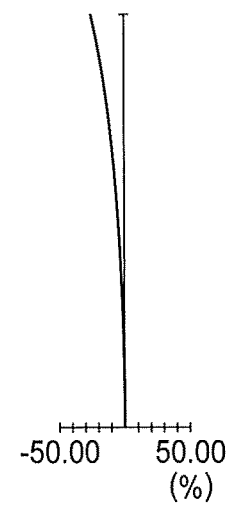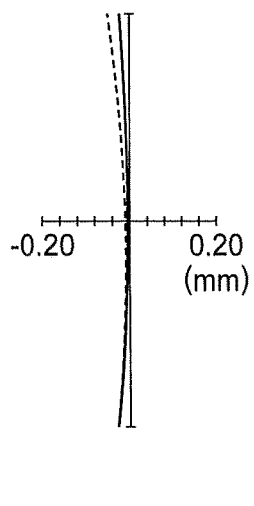

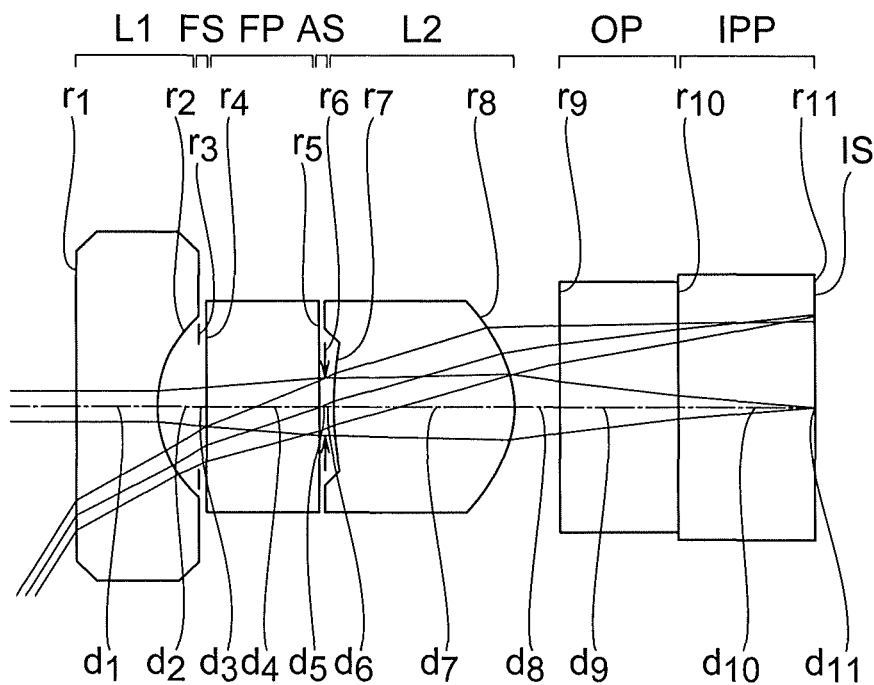
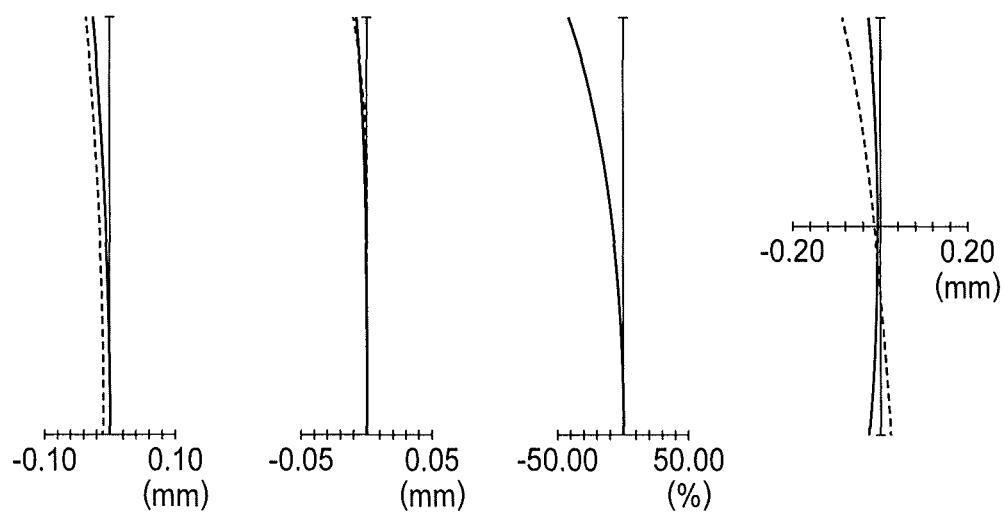

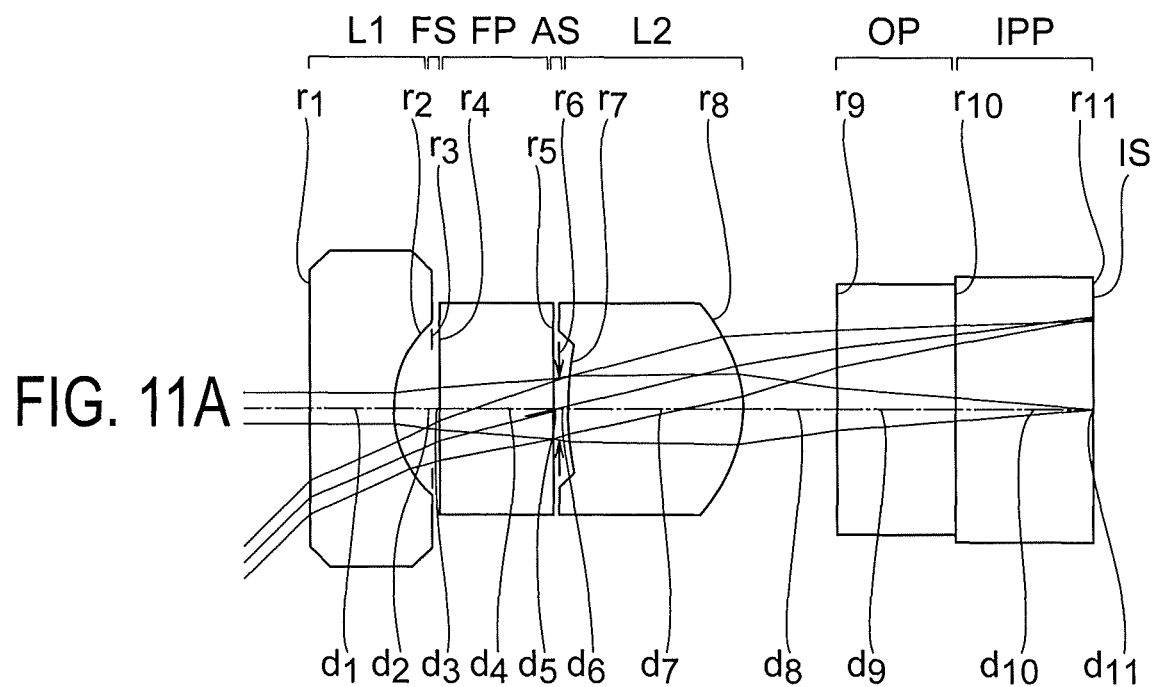
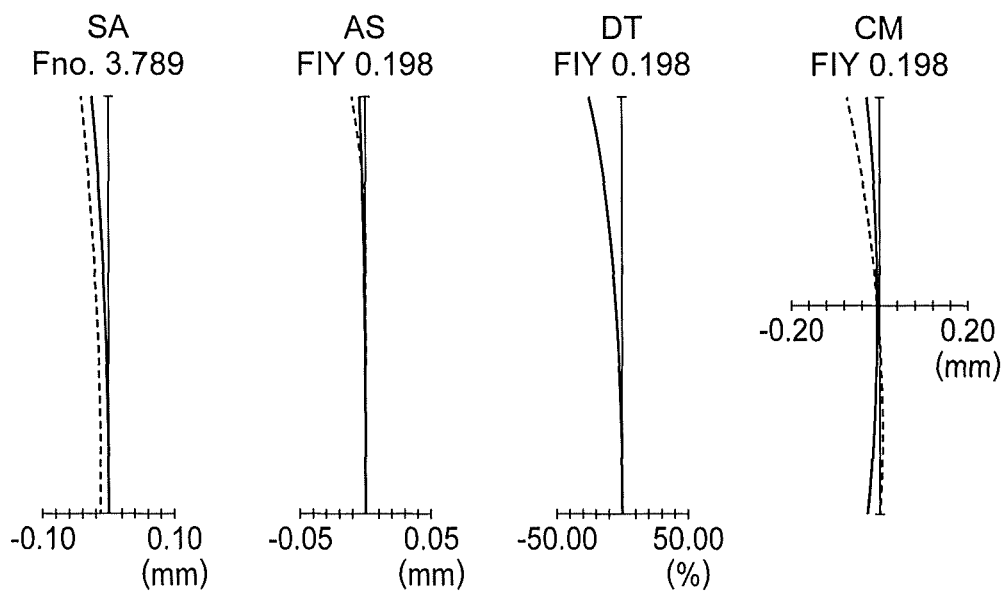

OBJECTIVE OPTICAL SYSTEM, ENDOSCOPE, AND ENDOSCOPE SYSTEM

CROSS-REFERENCE TO RELATED APPLICATION

The present application is a continuation application of PCT/JP2018/009232 filed on Mar. 9, 2018 which is based upon and claims the benefit of priority from Japanese Patent Application No. 2017-110422 filed on Jun. 2, 2017; the entire contents of which are incorporated herein by reference.

BACKGROUND

Technical Field

The present disclosure relates to an objective optical system, an endoscope, and an endoscope system, such as an endoscope objective optical system for medical treatment, an endoscope for medical treatment, and an endoscope system for medical treatment.

Description of the Related Art

A video scope has been known as an endoscope. In a video scope, an objective optical system and a solid state image sensor are disposed at a distal end of an insertion portion. An image of an object is acquired by capturing an image formed by the objective optical system by the imager.

With microminiaturization of the imager, extreme thinning of the insertion portion has been progressing in video endoscopes. With the progress in extreme thinning of the insertion portion, microminiaturization of the objective optical system becomes necessary.

For instance, widespread use of extremely thin video scopes having an outer diameter of the insertion portion not more than 4 mm has begun. In such extremely thin video scopes, an area in a plane orthogonal to an optical axis (hereinafter, referred to as 'cross-sectional area') is small. For example, a cross-sectional area of the imager and a cross-sectional area of the objective optical system is approximately 1 $mm^2$ or smaller than 1 $mm^2$.

Therefore, it is preferable that an objective optical system for an extremely thin video scope be an objective optical system with a short focal length. In the objective optical system with a short focal length, both an image height and the focal length are about 0.3 mm or less than 0.3 mm.

Moreover, an extremely thin video scope, while having an outer diameter not larger than 4 mm, is provided with a channel for treatment and a distal end bending mechanism to the insertion portion. In an extremely thin video scope having a distal end bending mechanism, a distal end side of the insertion portion can be bent. It is preferable that a length from a distal end up to a portion that can be bent (hereinafter, referred to as 'length of a distal end rigid portion') be short.

For shortening the length of the distal end rigid portion, an overall length of the objective optical system is sought to be short. For this, it is preferable that the objective optical system for extremely thin video scope be an objective optical system having a short overall length. The desirable overall length is 3 mm or shorter than 3 mm.

However, in an image pickup unit having an objective optical system and an imager, various optical elements other than lenses are disposed. For example, the optical elements include a sealing glass of the imager, a plane parallel plate for fixing the imager to a holding frame (hereinafter, referred to as 'flat plate for fixing'), and an optical filter. Therefore, securing a space for disposing these optical elements (hereinafter, referred to as 'predetermined space') in the image pickup unit, has to be taken into consideration.

In an objective optical system having a short focal length, such as an objective optical system having a focal length of about 0.3 mm, when the optical system includes only positive lenses, it becomes difficult to secure the predetermined space in the image pickup unit.

Since the sealing glass and the flat plate for fixing are disposed near an image plane in the image pickup unit, a space near the image plane corresponds to the predetermined space. Therefore, a long back focus is sought for the objective optical system having a short focal length.

As an optical system capable of securing a long back focus, an optical system of a retro focus type is available. Therefore, in the objective optical system having a short focal length, it is desirable to adopt the optical system of a retro focus type as an optical system. By adopting the optical system of retro focus type as an optical system, it is possible to secure the predetermined space.

Moreover, since the optical filter is disposed in the objective optical system, a space in the objective optical system corresponds to the predetermined space. Therefore, it is necessary to make the overall length of the optical system long to certain extent. However, as mentioned above, in the objective optical system of an extremely thin video scope, the overall length of the optical system is sought to be short.

For securing the predetermined space as well as shortening the overall length of the optical system, the number of lenses has to be reduced to the minimum number of lenses necessary. Therefore, in an objective optical system having a short focal length, it is desirable that the optical system include one negative lens and one positive lens.

Incidentally, in a video scope, an observation by narrow-band light has been widely used. Therefore, even in an extremely thin video scope, the narrow-band light observation is carried out.

In the narrow-band light observation, as compared to a white light observation, a contrast is improved in observation of a blood vessel and observation of a structure of a superficial portion of the mucous membrane. The improvement in the contrast is attributed to use of light of a wavelength band on a short-wavelength side of a wavelength band of white light (visible light). The narrow-band light observation is a method which is effective for observation of a blood vessel and observation of the structure of the superficial portion of the mucous membrane.

However, in a video scope, observation of parts other than the blood vessel, and the structure of the superficial portion of the mucous member, is also carried out. In this observation, the white light observation is used. Accordingly, in the optical system which enables the narrow-band light observation, it is necessary that it enabled to carry out the white light observation. In an objective optical system which enables the narrow-band light observation, it is sought that a longitudinal chromatic aberration is corrected favorably.

When the longitudinal chromatic aberration is large, there occurs a difference in focus at the time of white light observation and at the time of narrow-band light observation. In this case, one of an image by the white light observation and an image by the narrow-band light observation becomes an image having a low contrast.

For instance, for the observation of the superficial portion of the mucous member, the white light observation is to be carried out first and then the narrow-band light observation is to be carried out. In the white observation, the focusing is to be carried out for the superficial portion of the mucous member. Therefore, an image of the superficial portion of the mucous member with a high contrast is achieved.

Next, the observation is to be switched from the white light observation to the narrow-band light observation. At this time, when the longitudinal chromatic aberration is large, in the narrow-band light observation, the superficial portion of the mucous member is substantially out of focus. Therefore, in the narrow-band light observation, it is not possible to achieve an image other than an image of the superficial portion of the mucous member with a low contrast.

By imparting a focusing function to the objective optical system, it is possible to eliminate the focal shift. However, when the focusing function is imparted to the objective optical system, the optical system becomes large. Particularly, in an objective optical system for an extremely thin video scope, it is difficult to impart the focusing function.

For such reasons, in the objective optical system for the extremely thin video scope, the longitudinal chromatic aberration has to be corrected favorably with the required minimum number of lenses.

An objective optical system which includes one negative lens and one positive lens is disclosed in Japanese Patent Application Laid-open Publication No. Hei 5-341185, Japanese Patent Application Laid-open Publication No. Hei 7-318799, International Unexamined Patent Application Publication No. 2015/122261, and Japanese Patent Application Laid-open Publication No. 2009-288682.

SUMMARY

An objective optical system according to at least some embodiments of the present disclosure consisting of, in order from an object side to an image side:

a first lens having a negative refractive power,
an aperture stop, and
a second lens having a positive refractive power, wherein
an image-side surface of the first lens is concave toward the image side,
an image-side surface of the second lens is convex toward the image side, and
following conditional expressions (1), (2), (3), (4), (5), (6), and (7) are satisfied:

$$0.6 < LL1is/LsL2i < 1.25 \quad (1)$$

$$-3 < (LL1is/RL1i) \times (LsL2i/RL2i) < -1.25 \quad (2)$$

$$-2 < fL2^2/(f \times fL1) < -1.35 \quad (3)$$

$$2 < (nd1-1.63) \times (vd1-31) \quad (4)$$

$$5 < (n2-1.45) \times (vd2-31) \quad (5)$$

$$1.63 < nd1, \text{ and, } 31 < vd1 \quad (6)$$

$$1.45 < nd2, \text{ and, } 31 < vd2 \quad (7).$$

where,

LL1is denotes an air conversion length from the image-side surface of the first lens up to the aperture stop,
LsL2i denotes a distance from the aperture stop up to the image-side surface of the second lens,
RL1i denotes a radius of curvature of the image-side surface of the first lens,
RL2i denotes a radius of curvature of the image-side surface of the second lens,
fL1 denotes a focal length of the first lens,
fL2 denotes a focal length of the second lens,
f denotes a focal length of the objective optical system,
nd1 denotes a refractive index for a d-line of the first lens,
vd1 denotes Abbe number for the first lens,
nd2 denotes a refractive index for the d-line of the second lens, and
vd2 denotes Abbe number for the second lens.

Moreover, an endoscope according to at least some embodiments of the present disclosure includes:

the abovementioned objective optical system, and
an image sensor which captures an image formed by the objective optical system.

Furthermore, an endoscope system according to at least some embodiments of the present disclosure includes:

the abovementioned endoscope, and
an image processor, wherein
the endoscope has a memory which stores data for image correction,
the data for image correction includes magnification correction data created on the basis of design data of the objective optical system,
the magnification correction data is data for correcting a lateral chromatic aberration in an image captured by the image sensor, and
the image processor corrects the lateral chromatic aberration on the basis of the magnification correction data, for not less than one of an R-band, a G-band, and a B-band.

BRIEF DESCRIPTION OF THE DRAWINGS

FIG. 2A is a cross-sectional view showing an arrangement of an objective optical system according to an example 1, and FIG. 2B, FIG. 2C, FIG. 2D, and FIG. 2E are aberration diagrams for the objective optical system according to the example 1;

FIG. 8A is a cross-sectional view showing an arrangement of an objective optical system according to an example 7, and FIG. 8B, FIG. 8C, FIG. 8D, and FIG. 8E are aberration diagrams for the objective optical system according to the example 7;

FIG. 9A is a cross-sectional view showing an arrangement of an objective optical system according to an example 8, and FIG. 9B, FIG. 9C, FIG. 9D, and FIG. 9E are aberration diagrams for the objective optical system according to the example 8;

FIG. 10A is a cross-sectional view showing an arrangement of an objective optical system according to an example 9, and FIG. 10B, FIG. 10C, FIG. 10D, and FIG. 10E are aberration diagrams for the objective optical system according to the example 9;

FIG. 11A is a cross-sectional view showing an arrangement of an objective optical system according to an example 10, and FIG. 11B, FIG. 11C, FIG. 11D, and FIG. 11E are aberration diagrams for the objective optical system according to the example 10;

DETAILED DESCRIPTION

Figure 1:
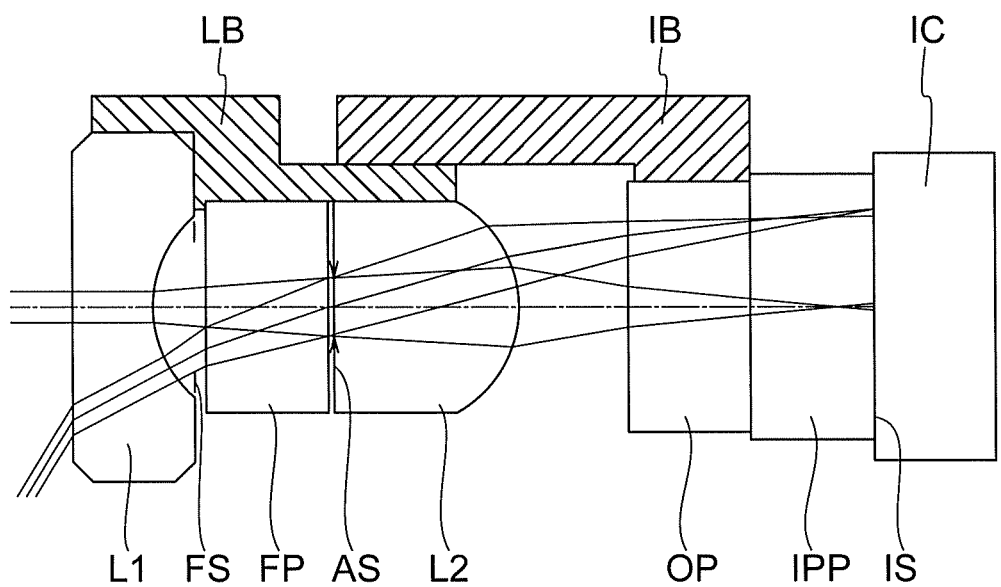
FIG. 1 is a cross-sectional view showing a basic arrangement of an objective optical system of the present embodiment.
Figure 3A:
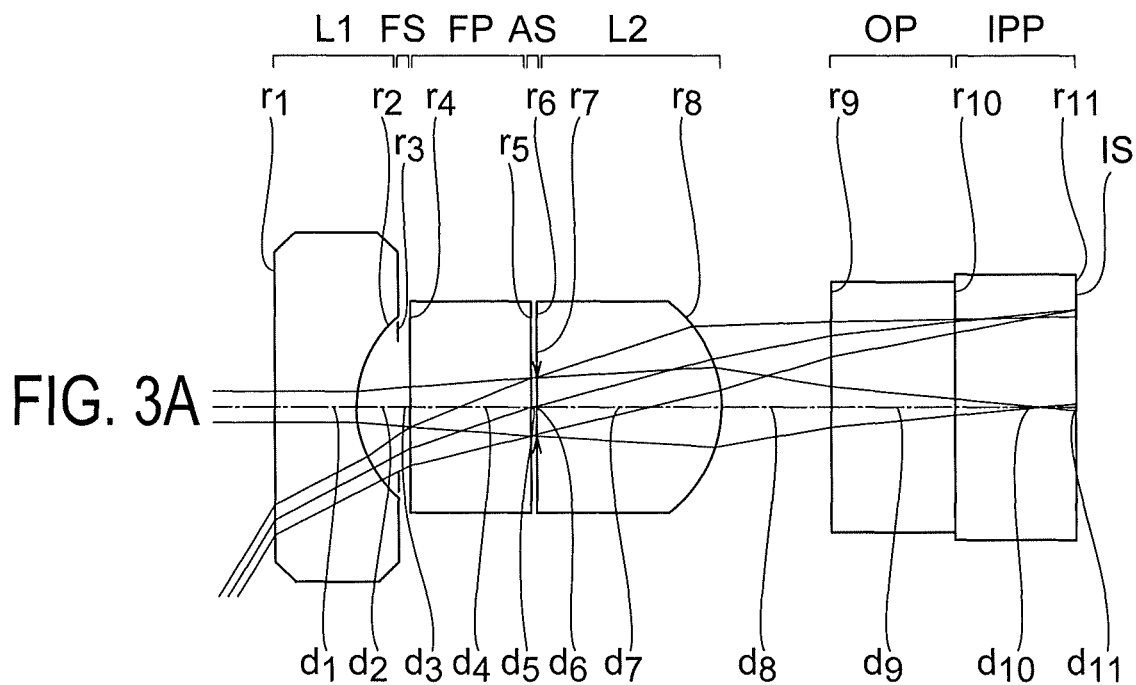
FIG. 3A is a cross-sectional view showing an arrangement of an objective optical system according to an example 2.
Figure 3B:
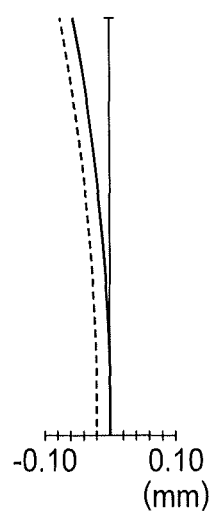
FIG. 3B, FIG. 3C, FIG. 3D, and FIG. 3E are aberration diagrams for the objective optical system according to the example 2.
Figure 3C:
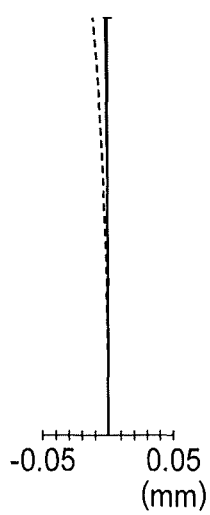
Figure 3D:
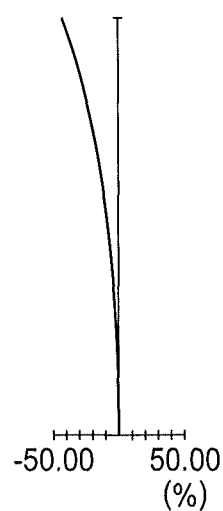
Figure 3E:
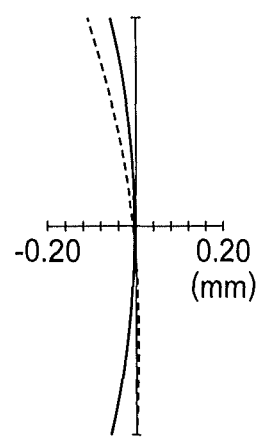
Figure 4A:
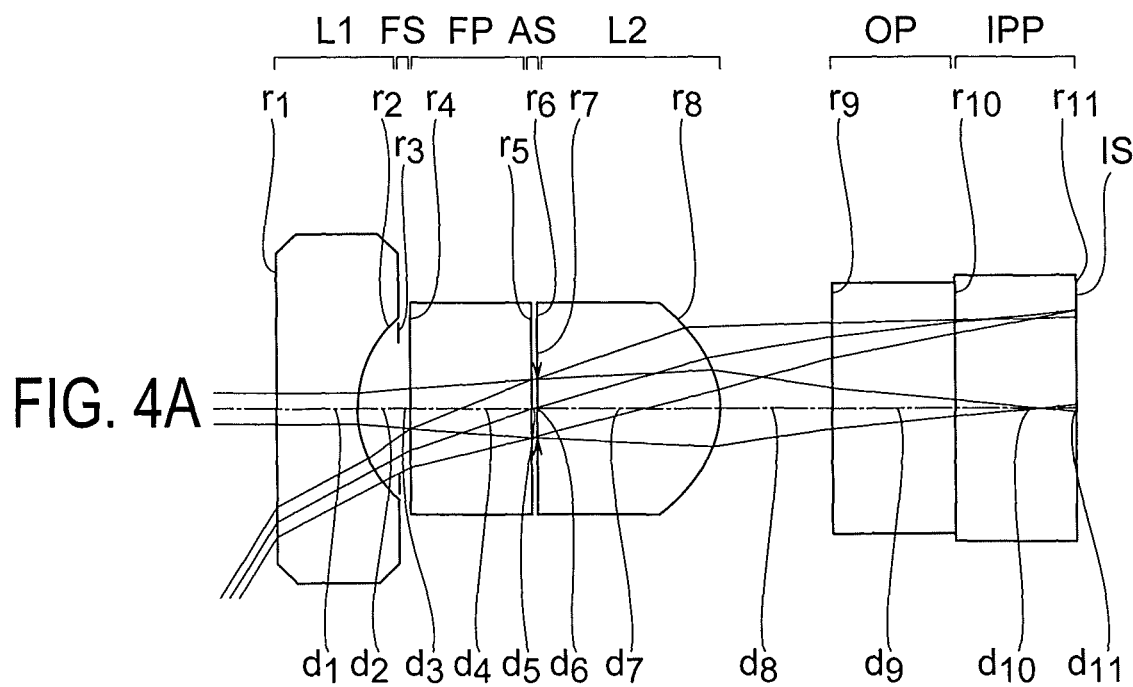
FIG. 4A is a cross-sectional view showing an arrangement of an objective optical system according to an example 3.
Figure 4B:
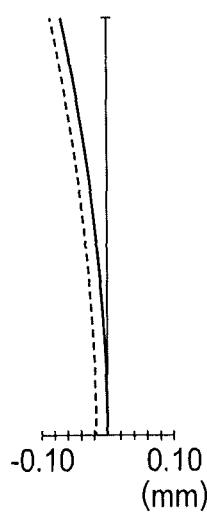
FIG. 4B, FIG. 4C, FIG. 4D, and FIG. 4E are aberration diagrams for the objective optical system according to the example 3.
Figure 4C:
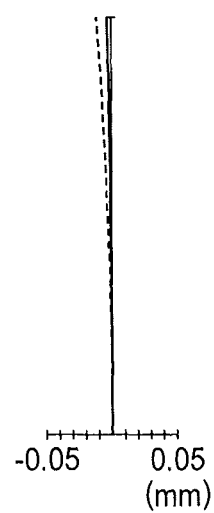
Figure 4D:
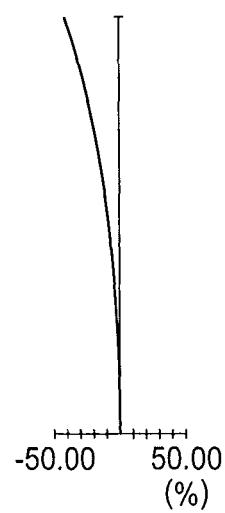
Figure 4E:
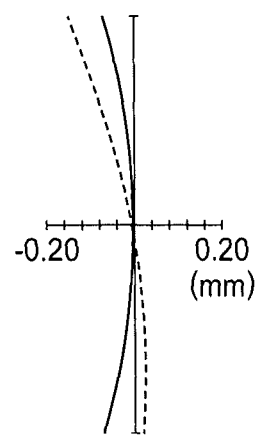
Figure 5A:
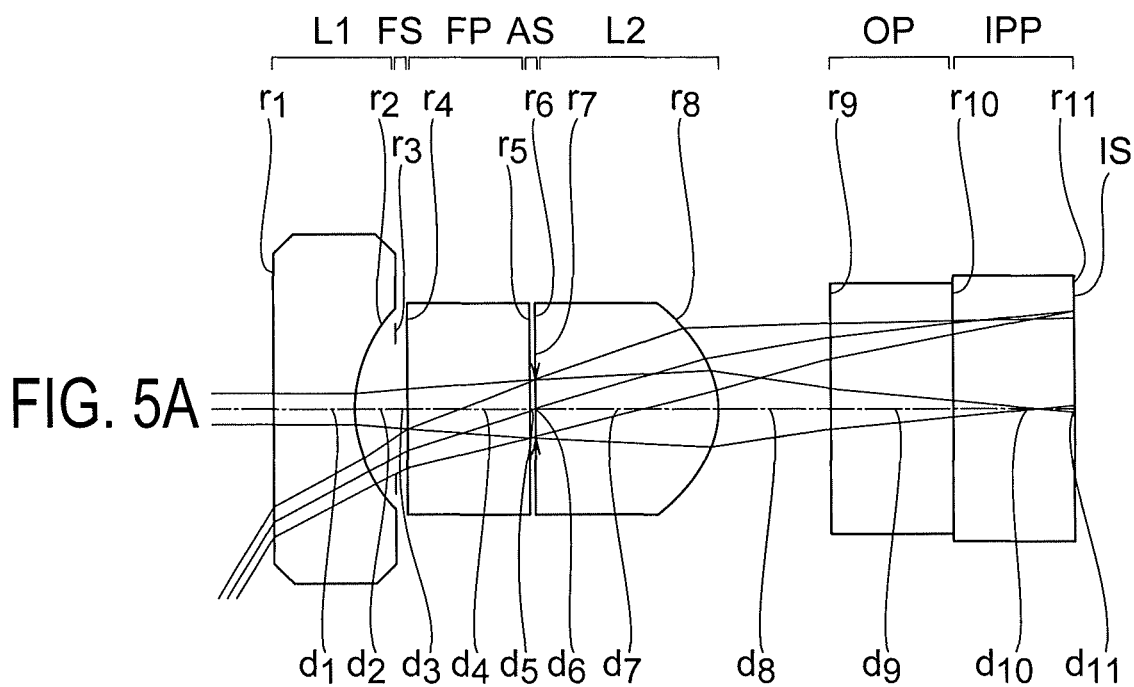
FIG. 5A is a cross-sectional view showing an arrangement of an objective optical system according to an example 4.
Figure 5B:
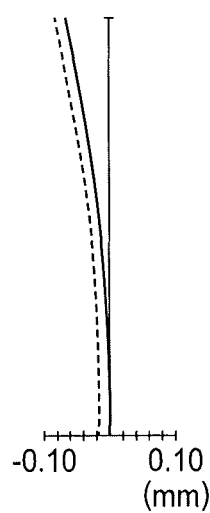
FIG. 5B, FIG. 5C, FIG. 5D, and FIG. 5E are aberration diagrams for the objective optical system according to the example 4.
Figure 5C:
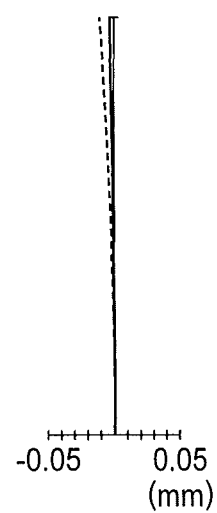
Figure 5D:
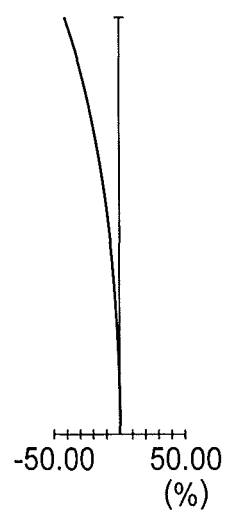
Figure 5E:
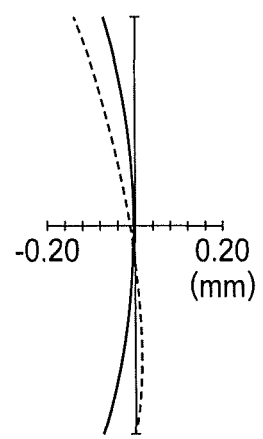
Figure 6A:
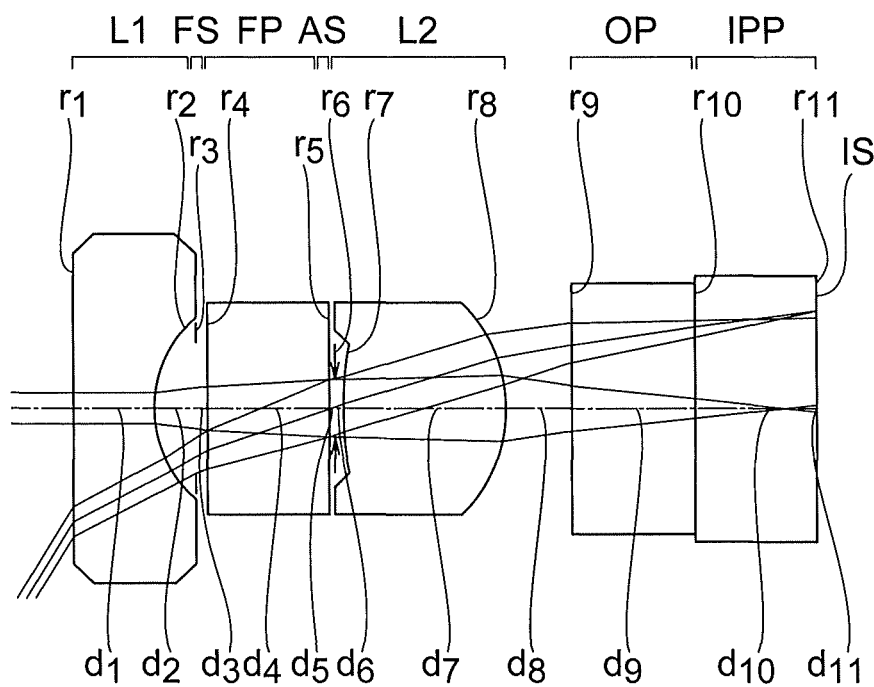
FIG. 6A is a cross-sectional view showing an arrangement of an objective optical system according to an example 5.
Figure 6B:
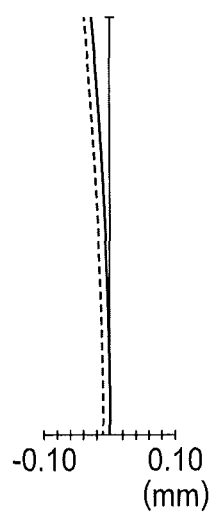
FIG. 6B, FIG. 6C, FIG. 6D, and FIG. 6E are aberration diagrams for the objective optical system according to the example 5.
Figure 6C:
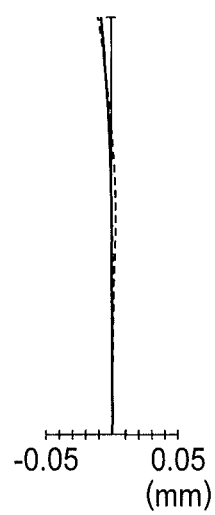
Figure 6D:
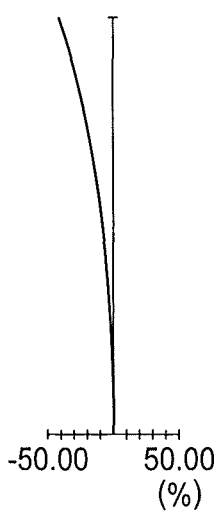
Figure 6E:
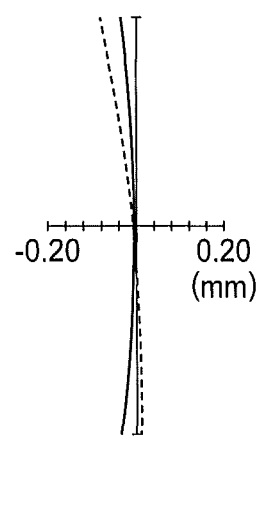
Figure 7A:
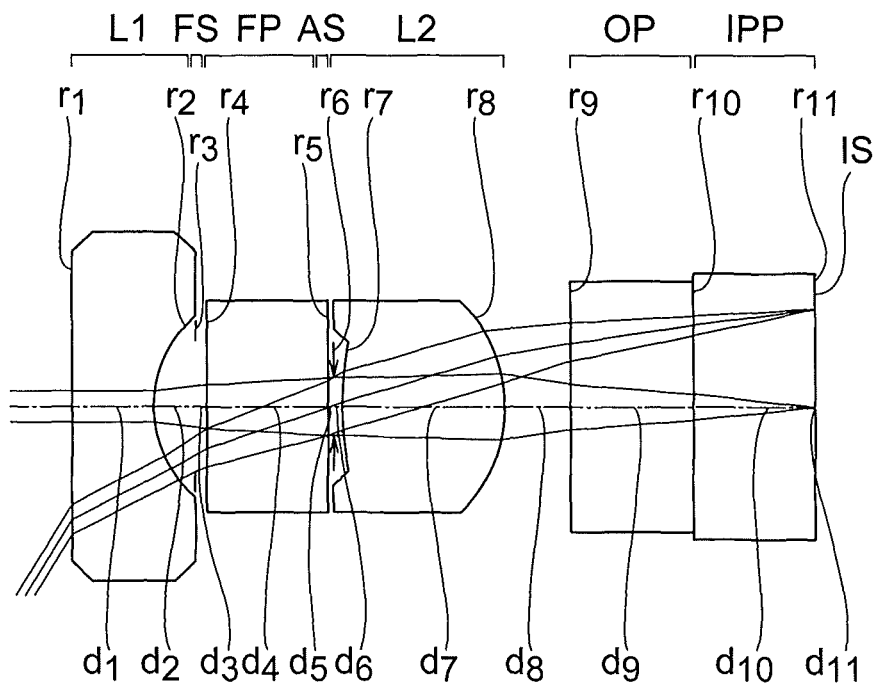
FIG. 7A is a cross-sectional view showing an arrangement of an objective optical system according to an example 6.
Figure 7B:
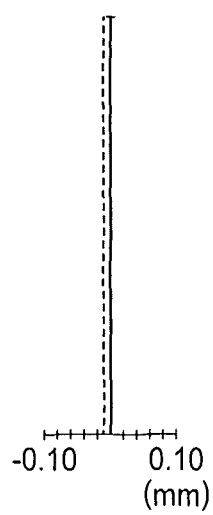
FIG. 7B, FIG. 7C, FIG. 7D, and FIG. 7E are aberration diagrams for the objective optical system according to the example 6.
Figure 7C:
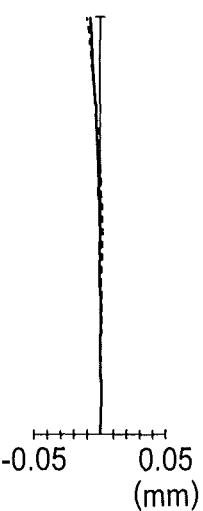
Figure 7D:
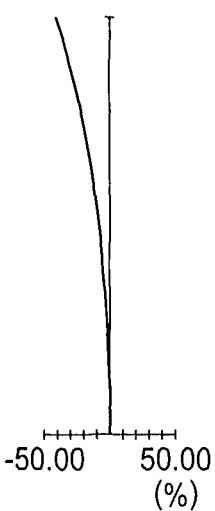
Figure 7E:
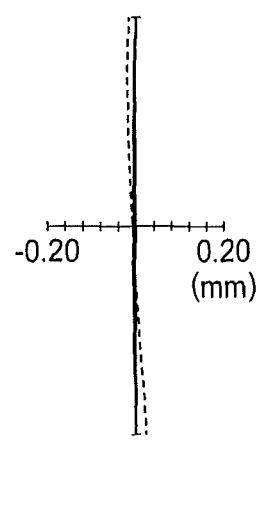

Reasons for and effects of an objective optical system, an endoscope, and an endoscope system according to the present embodiment having such arrangement will be described below by referring to the accompanying diagrams. However, the present disclosure is not restricted to the objective optical system, the endoscope, and the endoscope system according to the present embodiment.

The objective optical system of the present embodiment includes in order from an object side to an image side, a first lens having a negative refractive power, an aperture stop, and a second lens having a positive refractive power, wherein an image-side surface of the first lens is concave toward the image side, an image-side surface of the second lens is convex toward the image side, and following conditional expressions (1), (2), (3), (4), (5), (6), and (7) are satisfied:

$$0.6 < LL1is/LsL2i < 1.25 \quad (1)$$

$$-3 < (LL1is/RL1i) \times (LsL2i/RL2i) < -1.25 \quad (2)$$

$$-2 < fL2^2/(f \times fL1) < -1.35 \quad (3)$$

$$2 < (nd1-1.63) \times (vd1-31) \quad (4)$$

$$5 < (n2-1.45) \times (vd2-31) \quad (5)$$

$$1.63 < nd1, \text{ and, } 31 < vd1 \quad (6)$$

$$1.45 < nd2, \text{ and, } 31 < vd2 \quad (7).$$

where,

LL1is denotes an air conversion length from the image-side surface of the first lens up to the aperture stop, LsL2i denotes a distance from the aperture stop up to the image-side surface of the second lens, RL1i denotes a radius of curvature of the image-side surface of the first lens, RL2i denotes a radius of curvature of the image-side surface of the second lens, fL1 denotes a focal length of the first lens, fL2 denotes a focal length of the second lens, f denotes a focal length of the objective optical system, nd1 denotes a refractive index for a d-line of the first lens, vd1 denotes Abbe number for the first lens, nd2 denotes a refractive index for the d-line of the second lens, and vd2 denotes Abbe number for the second lens.

The objective optical system of the present embodiment includes in the order from the object side, the first lens having a negative refractive power, the aperture stop, and the second lens having a positive refractive power.

Since the objective optical system includes two lenses, it is possible to make an overall length of the optical system short. Moreover, the negative lens being disposed on the object side and the positive lens being disposed on the image side, the optical system of a retro focus type is adopted as an optical system. Therefore, it is possible to secure a long back focus.

In such manner, in the objective optical system of the present embodiment, the long back focus is secured as well as the overall length of the optical system is shortened. Therefore, it is possible to use the objective optical system of the present embodiment as a microminiature objective optical system. The microminiature objective optical system is an optical system having a focal length of about 0.3 mm or smaller than 0.3 mm, and the overall length of 3 mm or smaller than 3 mm.

Furthermore, in the objective optical system of the present embodiment, it is preferable that conditional expressions (1), (2), (3), (4), (5), (6), and (7) be satisfied.

Conditional expression (1) is a conditional expression in which a relationship of the distance from the image-side surface of the first lens up to the aperture stop and the distance from the aperture stop up to the image-side surface of the second lens is regulated. Conditional expression (2) is a conditional expression in which a relationship of the radius of curvature of the image-side surface of the first lens, the radius of curvature of the image-side surface of the second lens, and the distance from the aperture stop up to each image-side surface is regulated. Both conditional expressions (1) and (2) are conditional expressions for the radius of curvature of lens surfaces and the distance from the lens surfaces up to the aperture to be appropriate correlated relationship.

In the objective optical system of the present embodiment, the image-side surface of the first lens is a surface which is concave toward the image side. Moreover, the image-side surface of the second lens is a surface which is convex toward the image side.

In both the first lens and the second lens, when the radius of curvature of the image side surface is made smaller than the radius of curvature of the object-side surface, almost all the refractive power of the overall optical system is concentrated in the image-side surface of the first lens and the image-side surface of the second lens. Consequently, an asymmetry of refraction at each image-side surface has a large effect on an occurrence of an astigmatism and an occurrence of a coma.

A principal light ray travels through a center of the aperture stop. When lens surfaces are disposed such that a center of curvature of lens surfaces coincide with the center of the aperture stop, the principal light ray is incident perpendicularly on the lens surface. In this case, the principal light ray is not refracted at the lens surface.

Whereas, light rays surrounding the principal light ray (hereinafter, referred to as 'subordinate light rays') are refracted at the lens surface. At this time, a symmetry of refraction is secured for a pair of subordinate light rays that face each other across the principal light ray. Consequently, there is almost no occurrence of the astigmatism and the coma.

In such manner, the arrangement of lens surfaces in which the center of curvature of lens surfaces coincides with the center of the aperture stop is an ideal arrangement for suppressing the occurrence of astigmatism and the occurrence of coma. Therefore, even in the objective optical system of the present embodiment, it is preferable to make the center of curvature of the image side surface and the center of the aperture stop coincide as far as possible.

The arrangement in which the center of curvature of the lens surface and the center of the aperture stop coincide is a concentric arrangement. The smaller the shift in the center of curvature of the lens surface and the center of the aperture stop, the higher is the concentricity.

As mentioned above, both conditional expressions (1) and (2) are conditional expressions for the radius of curvature of lens surfaces and the distance from the lens surfaces up to the aperture stop to be appropriate correlated relationship. Conditional expressions (1) and (2) can be said to be conditional expressions related to the concentricity.

The distance from the image-side surface of the first lens up to the aperture stop is a distance subjected to air conversion. In a case in which there is only air between the image-side surface of the first lens and the aperture stop, it is ideal to make a position of the aperture stop coincide with the center of curvature of the image-side surface of the first lens.

In a case in which there is not only air between the image-side surface of the first lens and the aperture stop, for example, in a case in which an optical filter is disposed, it is necessary that the distance from an apex of the image-side surface of the first lens up to the center of curvature is subjected to air conversion. In this case, it is ideal to make the position of the aperture stop in a state of being subjected to air conversion coincide with the center of curvature of the image-side surface of the first lens.

When such arrangement is made, since the principal light ray passes through the image-side surface of the first lens perpendicularly, no refraction of the principal light ray occurs at the image-side surface. In this state, since the symmetry of refraction of the subordinate light ray is secured, the astigmatism and the coma do not occur. Therefore, it is ideal to dispose the first lens and the aperture stop as mentioned above.

Moreover, at least a glass material of the second lens exists between the image-side surface of the second lens and the aperture stop. However, the distance from the image-side surface of the second lens up to the aperture stop is not subjected to air conversion.

In a case in which the aperture stop is positioned on an object-side surface of the second lens, the distance from the image-side surface of the second lens up to the aperture stop is only a thickness of the second lens. In a case in which the aperture stop is away from the object-side surface of the second lens, the distance from the image-side surface of the second lens up to the aperture stop is a distance from the object-side surface of the second lens up to the aperture stop added to the thickness of the second lens.

An angle of view of an optical system is expressed as an angle made by a principal light ray incident on the optical system and an optical axis. The angle of view of the optical system varies according to refraction of the principal light ray in the optical system. Therefore, for achieving the required angle of view, it is preferable to make an arrangement such that refraction of the principal light ray occurs in the optical system.

As mentioned above, when the center of curvature of the lens surface and the center of the aperture stop are made to coincide, the principal light ray is not refracted at the lens surface. In this case, it is not possible to achieve an effect of widening the angle of view using the refraction of the principal light ray. Therefore, it is desirable that the concentricity be determined upon taking into account the effect of widening the angle of view.

In conditional expression (1), LL1is denotes the air-conversion length from the image-side surface of the first lens up to the aperture stop. Here, LL1is, as mentioned above, corresponds to the distance from the image-side surface of the first lens up to the aperture stop after the air-conversion.

In a case in which nothing is disposed between the image-side surface of the first lens and the aperture stop, for LL1is, it is possible to use an actual distance as the air-conversion length.

However, as it will be described later, it is possible to dispose a plane parallel plate such as an optical filter between the image-side surface of the first lens and the aperture stop. In this case, only a thickness of the plane parallel plate is to be subjected to air conversion by using a refractive index of a material. Moreover, the thickness subjected to air conversion is included in LL1is.

Moreover, the aperture stop being formed by a thin plate, the aperture stop has a thickness. However, according to the optical notion, the aperture stop is deemed to be positioned on the second lens side. Therefore, the thickness of the aperture stop is to be included in LL1is.

In conditional expression (1), LsL2i is the distance from the aperture stop up to the image-side surface of the second lens. Here, LsL2i is a distance not subjected to air conversion.

In a case in which the aperture stop is positioned on the object-side surface of the second lens, a medium between the aperture stop and the image-side surface of the second lens is only the glass material of the second lens. In this case, the thickness of the second lens is not subjected to air conversion. For LsL2i, an actual distance not subjected to air conversion is used.

In a case in which the aperture stop is positioned on the object side of the object-side surface of the second lens, the glass material of the second lens and air exist between the aperture stop and the image-side surface of the second lens. Even in this case, the thickness of the second lens is not subjected to air conversion.

Description will be made envisaging that the medium between the image-side surface of the first lens and the aperture stop and the medium between the aperture stop and the image-side surface of the second lens are same. When it is assumed that LL1is and LsL2i are defined by the same medium, it is desirable that a position of the image-side surface of the first lens and a position of the image-side surface of the second lens be positions symmetric across the aperture stop. In other words, it is desirable that a relationship LL1is/LsL2i=1 be established.

With this assumption, when an absolute value of the radius of curvature of the image-side surface of the first lens and an absolute value of the radius of curvature of the image-side surface of the second lens are substantially same, it is possible to design as if the image-side surface of the first lens and the image-side surface of the second lens become a portion of a spherical surface or a portion of a substantially spherical surface in which the position of the aperture stop as a center of the sphere.

In such manner, when the image-side surface of the first lens and the image-side surface of the second lens are designed as if a portion of spherical surface positioned sandwiching the aperture stop, it is possible to design an optical system in which the refraction of the principal light ray at each image-side surface is small, and a symmetry of the refraction of the subordinate light rays is favorable.

However, practically, LsL2i is defined by the glass material of the second lens. Therefore, LL1is and LsL2i are not defined by the same medium. In this case, LsL2i becomes long due to an effect of the refractive index of the glass material of the second lens. Consequently, the most desirable value of numerical expression LL1is/LsL2i becomes smaller than 1 which is the most suitable value when the two media were assumed to be the same. Therefore, for the value of the numerical expression LL1is/LsL2i, it is preferable to set a desirable range around about 0.9 as a center.

When the value of the numerical expression LL1is/LsL2i falls below a lower limit value of conditional expression (1), LL1is becomes relatively small. In this case, for securing a high concentricity, a need to make the radius of curvature of the image-side surface of the first lens small arises. However, in a microminiaturized objective optical system, the radius of curvature of a concave surface is small in principle. Therefore, making the radius of curvature of the image-side surface of the first lens further smaller deteriorates workability. As a result, a favorable imaging performance is degraded. Therefore, it is not desirable that the value of numerical expression LL1is/LsL2i fall below the lower limit value of conditional expression (1).

To avoid the deterioration of workability, an arrangement has to be made such that the radius of curvature of the image-side surface of the first lens does not become small. However, in this case, the concentricity with respect to the aperture stop is degraded. Consequently, the astigmatism and the coma are deteriorated. Therefore, it is not desirable that the value of the numerical expression LL1is/LsL2i fall below the lower limit value of conditional expression (1).

When the absolute value of numerical expression LL1is/LsL2i exceeds an upper limit value of conditional expression (1), LsL2i becomes relatively small. In this case, for securing high concentricity, a need to make the radius of curvature of the image-side surface of the second lens small arises. However, in a microminiaturized objective optical system, the radius of curvature of a convex surface is small in principle. Therefore, making the radius of curvature of the image-side surface of the second lens further smaller deteriorates workability. As a result, a favorable imaging performance is degraded. Therefore, it is not desirable that the value of numerical expression LL1is/LsL2i exceed the upper limit value of conditional expression (1).

To avoid the deterioration of workability, an arrangement has to be made such that the radius of curvature of the image-side surface of the second lens does not become small. However, in this case, the concentricity with respect to the aperture stop is degraded. Consequently, the astigmatism and the coma are deteriorated. Therefore, it is not desirable that the value of numerical expression LL1is/LsL2i exceed the upper limit value of conditional expression (1).

It is preferable that the following conditional expression (1') is satisfied instead of conditional expression (1).

$$0.65 < LL1is/LsL2i < 1.15 \qquad (1')$$

Conditional expression (2) will be described below. Conditional expression (2) is a conditional expression regulating a radius of curvature of each image-side surface in an appropriate range with respect to LL1is and LsL2i regulated by conditional expression (1).

Regarding the radius of curvature RL1i of the image-side surface of the first lens, when the absolute value of numerical expression LL1is/RL1i is 1, it is concentric with respect to the aperture stop. Regarding the radius of curvature RL2i of the image-side surface of the second lens, when the absolute value of numerical expression LsL2i/RL2i is 1, it is concentric with respect to the aperture stop.

Numerical expression LL1is/RL1i and numerical expression LsL2i/RL2i can be said to be numerical expressions indicating a state of the two image-side surfaces. When an absolute value in a numerical expression obtained by multiplying two numerical expressions (LL1is/RL1i)×(LsL2i/RL2i) is 1, the concentricity of the two image-side surfaces with respect to the aperture stop is deemed as favorable.

However, it is preferable to set a desirable range of conditional expression (2) up on taking into consideration not only the concentricity but also the widening of an angle of view. For instance, the angle of view in general in a bronchial endoscope is about 120°. It is not desirable to narrow the angle of view which is the most basic optical specification, in return for the microminiaturization.

When the focal length is made short, the angle of view is widened. Therefore, theoretically, only by multiplying heretofore known optical design data by a proportional constant and reducing, it is possible to achieve optical design data with a widened angle of view. However, in a microminiaturized objective optical system, in a case in which the focal length is shortened by a simple task of reduction of the optical design data, the radius of curvature and a thickness of a lens decrease. Therefore, in such optical design data, in manufacturing of lens, degradation of workability and degradation of assemblability are induced. As a result, the imaging performance is degraded. In such manner, a design of a microminiaturized endoscope optical system is not simple.

When the absolute value of numerical expression LL1is/RL1i and the absolute value of numerical expression LsL2i/RL2i is 1, the principal light ray is not refracted at the image-side surface. Therefore, it is not possible to achieve an effect of widening the angle of view in which the image-side surface is used. Whereas, when the absolute value of numerical expression LL1is/RL1i and the absolute value of numerical expression LsL2i/RL2i is made higher than 1, it is possible to achieve the effect of widening the angle of view in which the image-side surface is used.

Therefore, in conditional expression (2), a desired range was determined such that the absolute value of numerical expression (LL1is/RL1i)×(LsL2i/RL2i) is higher than 1 and is not excessively higher than 1. In the present disclosure, the sign of the radius of curvature is positive in a case of having the center of curvature on the image side with respect to the surface, and is negative in a case of having the center of curvature on the object side with respect to the surface. Accordingly, RL1i becomes positive and RL2i becomes negative. Therefore, numerical expression (LL1is/RL1i)×(LsL2i/RL2i) becomes a negative value.

When the value of numerical expression (LL1is/RL1i)×(LsL2i/RL2i) falls below a lower limit value of conditional expression (2), either for one of the image-side surface of the first lens and the image-side surface of the second lens, or for both the image-side surface of the first lens and the image-side surface of the second lens, the concentricity with respect to the aperture stop is degraded. As a result, the astigmatism and the coma are deteriorated. Therefore, it is not desirable that the value of numerical expression (LL1is/RL1i)×(LsL2i/RL2i) fall below the lower limit value of conditional expression (2).

When the absolute value of numerical expression (LL1is/RL1i)×(LsL2i/RL2i) exceeds the upper limit value of conditional expression (2), either for one of the image-side surface of the first lens and the image-side surface of the second lens, or for both the image-side surface of the first lens and the image-side surface of the second lens, the refraction effect for the principal light ray is inadequate. As a result, widening the angle of view becomes difficult. Therefore, it is not desirable that the value of numerical expression (LL1is/RL1i)×(LsL2i/RL2i) exceed the upper limit value of conditional expression (2).

It is more preferable that the following conditional expression (2') is satisfied instead of conditional expression (2).

$$-2<(LL1is/RL1i)\times(LsL2i/RL2i)<-1.3 \qquad (2')$$

Conditional expression (3) will be described below. Conditional expression (3) is a conditional expression in which a desirable relation of the focal length of the first lens, the focal length of the second lens, and the focal length of the objective optical system is regulated by one numerical expression.

Lenses used in the objective optical system of the present embodiment are only two single lenses. Therefore, a correlation of these two lenses is extremely significant. In conditional expression (1), an appropriate condition for a positional relationship of the two lenses has been determined, and in conditional expression (2) an appropriate condition for the radius of curvature of the two lenses has been determined. In conditional expression (3), an appropriate condition for the refractive power of the two lenses is determined.

In an optical system including two lenses, the characteristic of the optical system is expressed by using a ratio of the focal length of the two lenses in many cases. However, the objective optical system of the present embodiment being microminiaturized, the focal length is extraordinarily short. The focal length is about 0.3 mm for example, or less than 0.3 mm.

The focal length of an optical system is nothing but a specification of that optical system. In an optical system which includes two lenses, dependence of focal length of the overall optical system and focal length of the two lenses is strong, and the focal length of the overall optical system has an extremely large effect on mounting. Therefore, for reflecting a relationship of these three focal lengths in one numerical expression, in conditional expression (3), numerical expression fL2²/(f×fL1) is determined.

Numerical expression fL2²/(f×fL1) is obtained by multiplying numerical expression (fL2/fL1) and (fL2/f). Numerical expression (fL2/fL1) is a ratio of focal lengths of the two lenses, and numerical expression (fL2/f) is a ratio of the focal length of the second lens to the focal length of the objective optical system.

It is desirable that an absolute value of numerical expression (fL2/fL1) be about 1. By making such arrangement, it is possible to balance the refractive power of the first lens and the refractive power of the second lens.

It is desirable that a value of numerical expression (fL2/f) be about 1.5. When such an arrangement is made, fL2 becomes relatively large. As a result, it is possible to secure an appropriate back focus.

Furthermore, it is preferable to regulate a relation of numerical expression (fL2/fL1) and numerical expression (fL2/f). It is not desirable that both the absolute value of numerical expression (fL2/fL1) and the absolute value of numerical expression (fL2/f) become large or become small.

In a case in which both the absolute values of two numerical expressions are large, the focal length of the second lens becomes excessively long with respect to the focal length of the first lens and the focal length of the objective optical system. Consequently, the overall length of the objective optical system becomes long. Therefore, it is not desirable that both the absolute values of two numerical expressions become excessively large.

In a case in which both the absolute values of two numerical expressions are small, the focal length of the second lens becomes excessively short with respect the focal length of the first lens and the focal length of the objective optical system. Consequently, it becomes difficult to secure an appropriate back focus. Therefore, it is not desirable that both the absolute values of two numerical expressions become excessively small.

As described above, a value of numerical expression fL2²/(f×fL1) falling below a lower limit value of conditional expression (3) corresponds to the focal length of the second lens becoming excessively long relatively. In this case, the overall length of the objective optical system becomes long. Therefore, it is not desirable that the value of numerical expression fL2²/(f×fL1) fall below the lower limit value of conditional expression (3).

The value of numerical expression fL2²/(f×fL1) exceeding an upper limit value of conditional expression (3) corresponds to the focal length of the second lens becoming excessively short relatively. In this case, it becomes difficult to secure an appropriate back focus. Therefore, it is not desirable that the value of numerical expression fL2²/(f×fL1) exceed the upper limit value of conditional expression (3).

It is more preferable that the following conditional expression (3') is satisfied instead of conditional expression (3).

$$-1.65<fL2^2/(f\times fL1)<-1.35 \qquad (3')$$

By satisfying conditional expression (3'), it is possible to further shorten the overall length of the optical system.

Conditional expressions (4) and (6) will be described below. Conditional expressions (4) and (6) are conditional expressions related to the refractive index of and Abbe number for the first lens.

For the first lens, it is desirable to use essentially a lens having a high refractive index and low dispersion. The higher the refractive index of the first lens, it is possible to make the radius of curvature of the image-side surface larger. Consequently, it is possible to make the workability of lens favorable. As a result, it is possible to secure a favorable imaging performance. Therefore, it is desirable that the refractive index of the first lens be high.

At the first lens, there is a strong tendency of the correction of a lateral chromatic aberration becoming inadequate. The lower the dispersion of the first lens, it is possible to suppress the tendency of the correction of the lateral chromatic aberration becoming inadequate. Therefore, it is desirable that the dispersion of the first lens be low.

At the first lens, there is a strong tendency of the correction of a longitudinal chromatic aberration becoming excessive. It is preferable to make the dispersion of the first lens high with respect to the correction of the longitudinal chromatic aberration. However, the negative effect due to deterioration of the lateral chromatic aberration is greater than the negative effect due to deterioration of the longitudinal chromatic aberration. Therefore, at the first lens, it is preferable to give priority to the correction of the lateral chromatic aberration over the correction of the longitudinal chromatic aberration. Therefore, it is desirable that the dispersion of the first lens be low.

Dispersion of an optical material used for a lens is prone to become high as the refractive index becomes high. This signifies that there is a limitation for achieving both of the high refractive index and low dispersion. Therefore, there is a limit to combinations of practical refractive index and dispersion. In selection of an optical material to be used for the first lens, the options are limited.

Numerical expression $(nd1-1.63) \times (vd1-31)$ in conditional expression (4) is a numerical expression indicating the balance of the refractive index and Abbe number. In conditional expression (4), by using this numerical expression, a preferable range of the refractive index and a preferable range of Abbe number are regulated.

In this numerical expression, as conditional expression (6) is satisfied such that a value of nd1 and a value of vd1 exceed respective reference values, and as the value of nd1 and the value of vd1 become larger, a value of the numerical expression becomes large. Therefore, as the value of $(nd1-1.63) \times (vd1-31)$ becomes larger, an optical material to be used for the first lens has the characteristic of low dispersion while having a high refractive index. As a result, since it is possible to correct the lateral chromatic aberration favorably, it is possible to facilitate improvement in the imaging performance.

Even in a case of low refractive index and high dispersion when the value of nd1 and the value of vd1 fall below the respective reference values, conditional expression (4) may have a positive value. Therefore, it is necessary to satisfy conditional expression (6) together with conditional expression (4).

In a case in which one of the refractive index and Abbe number is extremely high and the other is low in this numerical expression, the value of numerical expression does not become large. In a case in which the value falls below a lower limit value mainly due to the low refractive index, a radius of curvature of an image-side concave surface becomes small and the workability is degraded. Moreover, in a case in which the value falls below the lower limit value mainly due to low Abbe number, the lateral chromatic aberration is deteriorated. In both the cases, the imaging performance of the optical system is degraded. Therefore, in this numerical expression, it is possible to express whether or not there is an improvement in the imaging performance of the optical system.

When the value of numerical expression $(nd1-1.63) \times (vd1-31)$ falls below the lower limit value of conditional expression (4), it leads to degradation of workability of the first lens and deterioration of the lateral chromatic aberration.

In a case in which the main cause of the value falling below the lower limit value of conditional expression (4) is low refractive index, the radius of curvature of the image-side surface of the first lens becomes small. Consequently, the workability of the first lens is degraded. As a result, the imaging performance is degraded.

In a case in which the main cause of the value falling below the lower limit value of conditional expression (4) is low Abbe number, it becomes difficult to suppress an occurrence of the lateral chromatic aberration. As a result, the lateral chromatic aberration is deteriorated.

In a case in which the main cause of the value falling below the lower limit value of conditional expression (4) is both the low refractive index and low Abbe number, the workability of the first lens is degraded as well as the lateral chromatic aberration is deteriorated.

Thus, it is not desirable that the value of numerical expression $(nd1-1.63) \times (vd1-31)$ fall below the lower limit value of conditional expression (4).

Conditional expressions (5) and (7) will be described below. Conditional expressions (5) and (7) are conditional expressions related to the refractive index and Abbe number for the second lens.

Even for the second lens, it is desirable to use essentially a lens having a high refractive index and low dispersion. The higher the refractive index of the second lens, it is possible to make the radius of curvature of the image-side surface larger. Consequently, it is possible to make the workability of the lens favorable. As a result, it is possible to secure a favorable imaging performance. Therefore, it is desirable that the refractive index of the second lens be high.

At the second lens, there is a strong tendency of correction of both the longitudinal chromatic aberration and the lateral chromatic aberration becoming inadequate. The lower the dispersion of the second lens, it is possible to suppress both the tendency of the correction of the longitudinal chromatic aberration becoming inadequate and the tendency of the correction of the lateral chromatic aberration becoming inadequate. Therefore, it is desirable that the dispersion of the second lens be low.

In the objective optical system of the present embodiment, the longitudinal chromatic aberration is corrected favorably. The second lens is a significant lens for improvement of the longitudinal chromatic aberration. Therefore, more significance is placed on Abbe number for the second lens than on Abbe number for the first lens.

Numerical expression $(nd2-1.45) \times (vd2-31)$ in conditional expression (5) resembles to numerical expression $(nd1-1.63) \times (vd1-31)$ in conditional expression (4). However, in conditional expression (5), the reference value for the refractive index is lowered to 1.45. By doing so, in conditional expression (5), it is possible to achieve an evaluated value in which more significance is placed on Abbe number.

Even in this numerical expression, as conditional expression (7) is satisfied such that a value of nd2 and a value of vd2 exceed respective reference values, and as the value of nd2 and the value of vd2 become larger, a value of the numerical expression becomes large. Therefore, as the value of $(nd2-1.45) \times (vd2-31)$ becomes larger, an optical material to be used for the second lens has the characteristic of having a comparatively high refractive index irrespective of whether or not the significance is placed on the low dispersion. In this case, it is possible to correct the longitudinal chromatic aberration and the lateral chromatic aberration favorably, and it is possible to correct particularly the longitudinal chromatic aberration more favorably. As a result, it is possible to facilitate the improvement in the imaging performance.

Even in a case of low refractive index and high dispersion when the value of nd2 and the value of vd2 fall below the respective reference values, conditional expression (5) may have a positive value. Therefore, it is necessary to satisfy conditional expression (7) together with conditional expression (5).

In a case in which one of the refractive index and Abbe number is extremely high and the other is low in this numerical expression, the value of numerical expression does not become large. In a case in which the value falls below the lower limit value mainly due to the low refractive index, a radius of curvature of an image-side convex surface becomes small and the workability is degraded. Moreover, in a case in which the value falls below a lower limit value mainly due to low Abbe number, the longitudinal chromatic aberration and the lateral chromatic aberration are deteriorated. In both cases, the imaging performance of the optical system is degraded. Therefore, in this numerical expression, it is possible to express whether or not there is an improvement in the imaging performance of the optical system.

When the value of numerical expression (nd2−1.45)× (vd2−31) falls below the lower limit value of conditional expression (5), it leads to degradation of workability of the second lens and deterioration of the longitudinal chromatic aberration and the lateral chromatic aberration.

In a case in which the main cause of the value falling below the lower limit value of conditional expression (5) is low refractive index, the radius of curvature of the image-side surface of the second lens becomes small. Consequently, the workability of the second lens is degraded. As a result, the imaging performance is degraded.

In a case in which the main cause of the value falling below the lower limit value of conditional expression (5) is low Abbe number, it becomes difficult to suppress the occurrence of the longitudinal chromatic aberration and the occurrence of the lateral chromatic aberration. As a result, the longitudinal chromatic aberration and the lateral chromatic aberration are deteriorated.

In a case in which the main cause of the value falling below the lower limit value of conditional expression (5) is both the low refractive index and low Abbe number, the workability of the second lens is degraded as well as the longitudinal chromatic aberration and the lateral chromatic aberration are deteriorated.

Optical crystals or optical glasses in a restricted sense are optical materials to be used for the lenses. Specific examples of the optical material, and whether or not each optical material satisfies conditional expressions (4) and (6) or conditional expressions (5) and (7) are shown below. A 'o' indicates that the material satisfies conditional expressions and a 'x' indicates that the material does not satisfy conditional expressions.

A specific example of optical crystals is sapphire. Specific examples of the optical glass are S-LAH92, S-LAH58, S-LAH66, S-LAM3, S-LAL7, and S-BAL35. All these optical glasses are optical glasses manufactured by Ohara Corporation.

| Name | Refractive Index nd | Abbe number vd | Conditional expressions (4) and (6) | Conditional expressions (5) and (7) |
| --- | --- | --- | --- | --- |
| Sapphire | 1.7682 | 71.79 | o | o |
| S-LAH92 | 1.8919 | 37.13 | x | x |
| S-LAH58 | 1.883 | 40.76 | o | x |
| S-LAH66 | 1.7725 | 34.97 | o | o |
| S-LAM3 | 1.717 | 47.92 | x | x |
| S-LAL7 | 1.6516 | 58.55 | x | o |
| S-BAL35 | 1.58913 | 61.14 | x | x |

The optical material used for the lens is not restricted to the optical crystals and optical glasses in a restricted sense. For instance, it is also possible to use an optical resin for the lenses. In this case, optical resins that can be used for the optical material of the first lens and the second lens are restricted to optical resins which satisfy conditional expressions (4) and (6) and conditional expressions (5) and (7). However, acrylic optical resins, polycarbonate optical resins, and polyolefin optical resins copiously used in lenses for consumer use do not satisfy conditional expressions (4) and (6) and conditional expressions (5) and (7).

In the objective optical system of the present embodiment, conditional expressions (1), (2) and (3) are satisfied. Therefore, it is possible to realize an appropriate arrangement related to the position, the radius of curvature, and the refractive power of the first lens and the second lens. Moreover, conditional expressions (4), (5), (6), and (7) are satisfied. Therefore, most suitable selection of optical materials for the first lens and the second lens is possible.

In such manner, the present embodiment is useful for realizing an appropriate arrangement of the microminiaturized objective optical system. Furthermore, by satisfying conditional expression (5) related to the optical material of the second lens, it is possible to further improve the longitudinal chromatic aberration, as compared to a conventional objective optical system which includes two lenses. The improvement of the longitudinal chromatic aberration will be described in detail in an example 1.

A specific example of an arrangement of the objective optical system of the present embodiment will be described below. FIG. 1 is a cross-sectional view showing an arrangement of an image pickup unit. The image pickup unit includes an object-side sub unit and an image-side sub unit.

The object-side sub unit includes the objective optical system of the present embodiment and a lens frame LB. The image-side sub unit includes an imager and an imager frame IB. An image pickup surface IS of the imager is positioned on an image plane of the objective optical system.

In the image pickup unit shown in FIG. 1, the objective optical system of the present embodiment includes in order from an object side, a first lens L1 having a negative refractive power, an aperture stop AS, and a second lens L2 having a positive refractive power. An image-side surface of the first lens L1 is a surface which is concave toward an image side. An image-side surface of the second lens L2 is a surface which is convex toward the image side.

In such manner, in the objective optical system of the present embodiment, the first lens L1 and the second lens L2 are the only two optical members having a refractive power. Accordingly, these two lenses bear the imaging performance of the objective optical system. Moreover, realization of optical specifications of the objective optical system is also carried out by these two lenses.

The feature of the objective optical system of the present embodiment is a point that securing an appropriate back focus, shortening the overall length of the optical system, and favorable correction of the longitudinal chromatic aberration are realized by two lenses. However, practically, the objective optical system does not include only two lenses. An optical member other than lens is disposed between the first lens and the second lens, or on the image side of the second lens.

In the image pickup unit shown in FIG. 1, a filter plate FP is disposed between the first lens L1 and the second lens L2. An optical plate OP for fixing a frame and an optical plate IPP for sealing the imager are disposed between the second lens L2 and the image pickup surface IS. An imager substrate IC is disposed on an opposite side of the optical plate OP, with the optical plate IPP interposed between the optical plate OP and the imager substrate IC.

In the image pickup unit, optical members having an effect on an optical performance are the first lens L1, the filter plate FP, the second lens L2, the optical plate OP, and the optical plate IPP. Each of the filter plate FP, the optical plate OP, and the optical plate IPP has a significant function.

The filter plate FP will be described below. As mentioned above, in a video scope, an image of an object is acquired by capturing an image formed by an objective optical system, by an imager. In the acquired image, it is necessary that the color of the object is reproduced as appropriately as possible.

The color of the object in an image is determined mainly by spectral transmittance characteristics of the image pickup unit, or in other words, spectral transmittance characteristics of the objective optical system, and spectral sensibility characteristics of the imager. The filter plate FP is an optical member necessary for imparting the desired spectral transmittance characteristics to the objective optical system.

A solid state image sensor is an example of the imager. The solid state image sensor has a high sensitivity in a red wavelength band and a near infrared wavelength band (hereinafter referred to as 'R-band' and 'NIR-band') as compared to a blue wavelength band and a green wavelength band (hereinafter, referred to as 'R-band' and 'G-band'). Here, the spectral transmittance of the objective optical system is almost constant from the B-band to the NIR band. In this case, in an acquired image, red color is more emphasized than the original color of the object.

In such case, the filter plate FP which absorbs light of the NIR-band is to be disposed in the objective optical system. By making such arrangement, in the acquired image, it is possible to weaken the emphasis of red color. As a result, it is possible to reproduce appropriately the original color of the object.

For the filter plate FP, it is possible to use an absorbing filter or a reflecting filter. In the reflecting filter, an interference film is stacked on a surface of a colorless transparent plate. When such reflecting filter is disposed in the objective optical system, it is possible to reflect light of an unnecessary wavelength band.

Moreover, in a video scope, a treatment by irradiation of laser light is carried out while observing an object. A light intensity of laser light used for the treatment is much higher than a light intensity of observation light. Therefore, when the treatment is carried out without making the light intensity of the laser light low, a state of saturated white (hereinafter, referred to as 'image saturation') occurs. When the image saturation occurs, it is not possible to observe the treatment.

In such case, the filter plate FP which selectively reflects the laser light for treatment is to be disposed in the objective optical system. By making such arrangement, it is possible to prevent the occurrence of image saturation. A multi-layer interference film which selectively reflects the laser light for treatment is formed on an optical surface of the filter plate FP. The multi-layer interference film has a peculiarity of having a high reflectance with respect to a wavelength band of the laser light for treatment.

In such manner, whether or not the filter plate FP has been disposed in the objective optical system has a significant effect on securing the appropriate spectral transmittance characteristics in the image pickup unit and securing an appropriate color reproduction in an acquired image.

The optical plate IPP will be described below. By the optical plate IPP, it is possible to prevent the dirt from being adhered to the image pickup surface and to protect the image pickup surface from moisture and contact. In such manner, the optical plate IPP is an optical member indispensable for the imager. The optical plate IPP is integrated with an imager substrate IC at the time of manufacturing the imager. The imager is shipped in a state of the optical plate IPP and the imager substrate IC integrated.

The optical plate OP will be described below. Generally, a shape of the image pickup surface IS is noncircular. Therefore, in the imager as a single body, it is difficult to make high a decentration accuracy with respect to a central axis of the imager frame IB. In the image-side unit, centering of the imager with respect to the imager frame IB and holding the imager by the imager frame IB are carried out via the optical plate OP.

For carrying out the centering and holding, the optical plate OP is made a circular flat plate, and a circular hole to fit the optical plate OP is formed on the imager frame IB. By making such arrangement, the accuracy of decentration of the optical plate OP and the imager frame IB is suppressed to a level of a fitting error. Therefore, just by inserting the optical plate OP into the imager frame IB, it is possible to make the central axis of the optical plate OP and the central axis of the imager frame IB coincide with high accuracy.

As mentioned above, the decentration accuracy of the optical plate OP and the imager frame IB is suppressed to the level of the fitting error. Therefore, when the centering and adhering of the optical plate OP and the imager is carried out in advance, by inserting the optical plate OP into the imager frame IB, it is possible to improve the decentration accuracy of the imager with respect to the central axis of the imager frame IB.

As it will be described later, the central axis of the imager frame IB can be deemed as an optical axis of the objective optical system. Therefore, it is possible to improve easily the decentration accuracy of the imager with respect to the optical axis.

Moreover, by a simple work of inserting the optical plate OP into the imager frame IB, it is possible to hold the imager by the imager frame IB. Therefore, it is possible to improve assemblability.

In such manner, by using the optical plate OP, it is possible to secure the high decentration accuracy as well as high assemblability.

An optical member contributes significantly to a restriction of mounting including a frame structure and a method of assembling. For describing a possibility of mounting on a distal end of an extremely thin insertion portion (hereinafter, referred to as 'microminiaturized mounting'), a description of a relationship of the optical member and the frame structure and a description of the method of assembling are indispensable. Therefore, the relationship of the optical member and the frame structure and the method of assembling will be described below by using the object-side sub unit and the image-side sub unit.

In the object-side sub unit, the first lens L1, the filter plate FP, and the second lens L2 are held directly by the lens frame LB. The filter plate FP is positioned between the first lens L1 and the second lens L2.

The aperture stop AS is formed by a thin plate. The aperture stop AS is positioned near an object-side surface of the second lens L2. In a case in which the aperture stop AS is positioned on the object-side surface of the second lens L2, it is possible to stick the aperture stop AS to the object side of the second lens L2. In this case, the aperture stop AS is held by the lens frame LB via the second lens L2.

A flare stop FS is formed by a thin plate. The flare stop FS is disposed for cutting off unnecessary light from an object. In FIG. 1, the flare stop FS is positioned between the first lens L1 and the filter plate FP.

In the image-side sub unit, the optical plate OP is held directly by the imager frame IB. The optical plate OP and the optical plate IPP are cemented. Moreover, the optical plate IPP and the imager substrate IC are cemented. The optical plate IPP and the imager substrate IC are held by the imager frame IB via the optical plate OP.

An outer peripheral surface of the first lens L1 is a circular cylindrical surface. A round hole for fitting the first lens L1 is formed on a left side of the lens frame LB. Both of an outer peripheral surface of the filter plate FP and an outer peripheral surface of the second lens L2 are circular cylindrical surfaces. A round hole for fitting the filter plate FP and the second lens L2 is formed on a right side of the lens frame LB.

A procedure for assembling the object-side sub unit will be described below. To start with, the flare stop FS and the first lens L1 are inserted into the left side of the lens frame LB. Thereafter, the lens frame LB and the first lens L1 are cemented to be watertight by a way of adhesion or soldering etc. Next, the filter plate FP, the aperture stop AS, and the second lens L2 are inserted into the right side of the lens frame LB. Thereafter, the lens frame LB and the second lens L2 are adhered.

With the abovementioned procedure, it is possible to realize holding of the objective optical system by the lens frame LB. Moreover, the first lens L1, the filter plate FP, and the second lens L2 are positioned accurately. Therefore, it is possible to prepare an objective unit in which the focal length of the objective optical system is determined accurately.

Both of the decentration accuracy of the first lens L1 and the lens frame LB and the decentration accuracy of the second lens L2 and the lens frame LB are suppressed to the level of fitting error. Therefore, a central axis of the lens frame LB can be deemed as the optical axis of the objective optical system.

A procedure for assembling the image-side sub unit will be described below. To start with, a position of the optical plate OP and a position of the imager are adjusted such that a center of an outer diameter of the optical plate OP and a center of image pickup of the image pickup surface IS coincide. When the adjustment is completed, the optical plate IPP and the optical plate OP are adhered by an optical adhesive. Thereafter, an optical plate OP is inserted into the right side of the imager frame IB. At this time, an adhesive is to be applied to an outer peripheral surface of the optical plate OP. By doing so, it is possible to fix the imager frame IB and the optical plate OP by adhering.

The shape of the image pickup surface IS is noncircular. Therefore, in the imager as a single body, it is difficult to make high the decentration accuracy with respect to the central axis of the imager frame IB. However, by assembling the image pickup unit with the procedure described above, it is possible to fix the imager to the imager frame IB with the adequate decentration accuracy.

A method for joining the object-side sub unit and the image-side sub unit will be described below. By joining the two units, the image pickup unit is complete. The object-side sub unit and the image-side sub unit are joined by joining the lens frame LB and the imager frame IB.

An outer peripheral surface of the lens frame LB is a circular cylindrical surface. A round hole for fitting the lens frame LB is formed on the left side of the imager frame IB. When such arrangement is made, the decentration accuracy of the lens frame LB and the imager frame IB is suppressed to the level of the fitting error. Therefore, just by inserting the lens frame LB into the imager frame IB, it is possible to make the central axis of the lens frame LB and the central axis of the imager frame IB coincide with high accuracy.

As mentioned above, the central axis of the lens frame LB can be deemed as the optical axis of the objective optical system. Moreover, the central axis of the lens frame LB and the central axis of the imager frame IB coincide with high accuracy. Therefore, the central axis of the imager frame IB can be deemed as the optical axis of the objective optical system. As a result, it is possible to improve easily the decentration accuracy of the imager with respect to the optical axis.

Moreover, when the structure is as described above, by moving the lens frame LB and the imager frame IB in an optical axial direction, it is possible to vary a distance between the second lens L2 and the optical plate OP. Consequently, focus adjustment is possible.

A space between the outer peripheral surface of the lens frame LB and an inner peripheral surface of the imager frame IB is extremely small. Therefore, at the time of focus adjustment, it is possible to make decentration of the object-side sub unit and the image-side sub unit small.

In the focus adjustment, an adhesive is applied to an fitting portion. Moreover, while observing an image, the object-side sub unit is moved in a state of the image-side sub unit fixed. The object-side sub unit is halted at a position at which a focused image is achieved, and thereafter, the adhesive is allowed to cure.

With the procedure described above, it is possible to provide an image pickup unit having an appropriate focus adjustment carried out, without depending on a manufacturing error of each optical member.

An optical arrangement based on the abovementioned frame structure assumption will be described below in detail.

An optical system of a retro focus type which includes a first lens L1 and a second lens L2 contributes largely in realizing all of function, quality, assemblability, and workability of components by a combination with the abovementioned frame structure.

An optical system which includes the first lens L1 and the second lens L2, being capable of securing a long back focus, enables to dispose an optical plate IPP and an optical plate OP, and moreover, enables to secure a space necessary for the focus adjustment. Accordingly, it is possible to secure a quality of optical components, such as decentration and focus, without high component accuracy and a high assembling accuracy being sought.

Furthermore, a region in which a light ray height is low and an inclination smaller than an inclination of a principal light ray in an object space is created between the first lens L1 and the second lens L2. Therefore, it is possible to dispose the filter plate FP between the two lenses. When it is possible to dispose the filter plate FP in the optical system, it is possible to fulfil optical requirements such as high color reproducibility and attenuation of light of a specific wavelength band.

In such manner, the objective optical system of the present embodiment does not pale at points such as assembling adjustment, component accuracy, and filter function, in comparison with an objective optical system of a large size. Therefore, the objective optical system of the present embodiment fulfils mounting requirement similar to that of the objective optical system of a large size in spite of being envisaged to be microminiaturized.

In the objective optical system of the present embodiment, it is preferable that the image-side surface of the second lens be an aspheric surface, and a curvature of the aspheric surface is smaller at a periphery than at a center.

It is preferable that the image-side surface of the second lens is an aspheric surface having a curvature smaller at the periphery than at the center. When such arrangement is made, it is possible to correct a spherical aberration.

In the objective optical system of the present embodiment, even when conditional expressions (1), (2), and (3) are satisfied, coma and astigmatism sill remain. By making the image-side surface of the second lens aspheric, it is possible to correct more favorably a residual coma and a residual astigmatism.

For instance, in a case in which priority is given to widening the angle of view and the absolute value of LsL2i/RL2i is made higher than 1, an absolute value of the radius of curvature RL2i on an axis of the aspheric surface becomes smaller than LsL2i. Consequently, near the axis, the concentricity for the aperture stop is lowered.

However, in the objective optical system of the present embodiment, the aspheric surface for which the curvature becomes smaller for the periphery than for the center is provided to the image-side surface of the second lens. Consequently, a position of a local position of the center of curvature at a peripheral portion of the image-side surface is brought closer toward the aperture stop. As a result, it is possible to suppress a refraction of a principal light ray at an off-axis image point. By this effect, it is possible to avoid degradation of the concentricity at the off-axis image point. As a result, it is possible to reduce the coma and the astigmatism.

In the objective optical system of the present embodiment, it is preferable that the second lens be a planoconvex lens.

In the objective optical system of the present embodiment, it is preferable that the second lens be a biconvex lens, and an object-side surface of the second lens be a surface which is convex toward the object side.

In the objective optical system of the present embodiment, it is preferable that the second lens be a biconvex lens, and an object-side surface of the second lens be a surface which is convex toward the object side, and the object-side surface of the second lens be an aspheric surface, and a curvature of the aspheric surface of the object-side surface is smaller at a periphery than at a center.

In the objective optical system of the present embodiment, it is preferable that the second lens be a convex meniscus lens, and an object-side surface of the second lens be an aspheric surface having a negative refractive power at a periphery.

In the objective optical system of the present embodiment, it is preferable that a material of the first lens be sapphire.

In an objective optical system, in order to improve durability with respect to sterilization, the first lens is fixed to the frame by soldering in some cases. While soldering, the lens may break due to expansion and contraction due to temperature variation. Therefore, a material of the lens is sought to have a high strength with respect to the expansion and contraction. Sapphire is a material having an extremely high strength. By using sapphire as a material of the lens, it is possible to solder the first lens to the frame.

In the objective optical system of the present embodiment, it is preferable that the material of the second lens be a low transition point glass with a transition point not more than 620° C.

In the objective optical system of the present embodiment, mainly an optical glass is envisaged as a material of the second lens. In a case in which the second lens is a planoconvex spherical lens, it is possible to manufacture by a procedure having steps of ball lens processing, surface grinding, and centering.

In a case of carrying out aberration correction more favorable than the aberration correction by the planoconvex spherical lens, refractive power is to be imparted to the object side of the second lens. By making such arrangement, it is possible to increase a degree of freedom of designing. However, grinding processing of a micro lens having a biconvex shape and a convex meniscus shape has a degree of difficult extremely high. Therefore, in a case of making a shape of the second lens a biconvex shape or a convex meniscus shape, manufacturing by glass molding is useful for manufacturing the second lens.

Moreover, in a case of using an aspheric surface for the image-side surface, cutting processing of the aspheric surface becomes a high-cost processing. Therefore, in a case of using an aspheric surface for the image-side surface of the second lens, manufacturing by glass molding is useful for manufacturing the second lens.

In glass molding, the lower the transition point of the material, the smaller is the load on the mold due to temperature. Therefore, in a case of selecting the glass molding for manufacturing the second lens, it is desirable to use a material having the transition point not higher than 620° C. of the material of the second lens.

Commercially available low transition point glasses, by and large, fulfil the condition of the transition temperature not higher than 620° C. Therefore, it is possible to use a low transition point glass as a material of the second lens.

An endoscope of the present embodiment includes the objective optical system of the present embodiment, and an image sensor which captures an image formed by the objective optical system.

An endoscope system of the present embodiment includes the endoscope of the present embodiment and an image processor, wherein the endoscope has a memory which stores data for image correction, the data for image correction includes magnification correction data created on the basis of design data of the objective optical system, the magnification correction data is data for correcting a lateral chromatic aberration in an image captured by the image sensor, and the image processor corrects the lateral chromatic aberration on the basis of the magnification correction data for at least one of an R-band, a G-brand, and a B-band.

One of the causes of degradation of a contrast of an image of the endoscope is the lateral chromatic aberration. Since only two lenses is used in the objective optical system of the present embodiment, the lateral chromatic aberration becomes an aberration which is difficult to correct.

Moreover, the objective optical system of the present embodiment does not include a lens which causes a reverse correction of the lateral chromatic aberration, for example a cemented lens. Consequently, in the objective optical system of the present embodiment, the lateral chromatic aberration is prone to be corrected inadequately. Furthermore, the lateral chromatic aberration which is prone to be corrected inadequately occurs almost in proportion to an image height.

An image having the lateral chromatic aberration is captured by the imager. The captured image has the lateral chromatic aberration.

The lateral chromatic aberration is a difference in imaging magnification according to color. In an image having the lateral chromatic aberration, a size of an image of an object differs for each of the R-band, the G-band, and the B-band. Therefore, by carrying out either electrical image enlargement or electrical image reduction for each band, it is possible to correct the lateral chromatic aberration.

The objective optical system of the present embodiment has the image processor. Therefore, when the electrical image enlargement or the electrical image reduction is carried out for each band in the image processor, it is possible to correct the lateral chromatic aberration appropriately. The image processor is also called as a video processor.

In an electrical correction of the lateral chromatic aberration, the data for image correction is used. The data for image correction is stored in a memory provided to the endoscope. The data for image correction includes the magnification correction data which is created on the basis of the design data of the objective optical system. The magnification correction data is data for correcting the lateral chromatic aberration in an image captured by the imager.

The magnification correction data depends on the design data of the objective optical system. Therefore, it is desirable that the magnification correction data be in pair with the objective optical system. It is desirable to store magnification correction data in the memory of the endoscope.

When the endoscope is connected to the image processor, the image processor reads identification data of the objective optical system from the endoscope. Thereafter, the image processor reads the magnification correction data that is in pair with the objective optical system from the endoscope. The electrical image enlargement or the electrical image reduction is carried out for each band on the basis of the magnification correction data. In the electrical image enlargement or the electrical image reduction, a linear magnification or a linear reduction is carried out.

For one or more of the R-band, the G-band, and the B-band, correction of the lateral chromatic aberration based on the magnification correction data is carried out. Therefore, in the electrical correction of the lateral chromatic aberration, it is not necessary to carry out the electrical image enlargement or the electrical image reduction for all of the R-band, the G-band, and the B-band.

For instance, one reference band for which no electrical image enlargement or no electrical image reduction is carried out may be provided, and the electrical image enlargement or the electrical image reduction may be carried out for the remaining two bands. Or, the electrical image enlargement or the electrical image reduction may be carried out for only a band with a large lateral chromatic aberration with respect to the reference band.

Examples of the objective optical system will be described below in detail by referring to the accompanying diagrams. However, the present disclosure is not restricted to the examples described below.

In lens cross-sectional views of the examples will be described below. FIG. 2A, FIG. 3A, FIG. 4A, FIG. 5A, FIG. 6A, FIG. 7A, FIG. 8A, FIG. 9A, FIG. 10A, and FIG. 11A show lens cross-sectional views. In the lens cross-sectional views of the examples, a light ray reaching the maximum image height and an axial image are shown.

Aberration diagrams of the examples will be described below.

FIG. 2B, FIG. 3B, FIG. 4B, FIG. 5B, FIG. 6B, FIG. 7B, FIG. 8B, FIG. 9B, FIG. 10B, and FIG. 11B show a spherical aberration (SA).

FIG. 2C, FIG. 3C, FIG. 4C, FIG. 5C, FIG. 6C, FIG. 7C, FIG. 8C, FIG. 9C, FIG. 10C, and FIG. 11C show an astigmatism (AS).

FIG. 2D, FIG. 3D, FIG. 4D, FIG. 5D, FIG. 6D, FIG. 7D, FIG. 8D, FIG. 9D, FIG. 10D, and FIG. 11D shows a distortion (DT).

FIG. 2E, FIG. 3E, FIG. 4E, FIG. 5E, FIG. 6E, FIG. 7E, FIG. 8E, FIG. 9E, FIG. 10E, and FIG. 11E show a coma (CM).

Moreover, in each aberration diagram, a horizontal axis indicates an aberration amount. The unit of aberration amount is mm for the spherical aberration, the astigmatism, and the coma. Moreover, the unit of aberration amount is % for the distortion. The unit of the image height is mm. Fno denotes an F-number. The unit of wavelength of an aberration curve is nm. The spherical aberration shows two aberrations which are an aberration of a d-line (solid line) and an aberration for a g-line (broken line). The astigmatism shows two aberrations which are a meridional aberration (broken line) and a sagittal aberration (solid line).

Example 1

An objective optical system of an example 1 will be described below. The objective optical system of the example 1 includes in order from an object side, a planoconcave negative lens L1 having a flat surface directed toward the object side, an aperture stop AS, and a planoconvex positive lens L2 having a flat surface directed toward the object side. The aperture stop AS is positioned on an object-side surface of the planoconvex positive lens L2. The planoconcave negative lens L1 is a first lens and the planoconvex positive lens L2 is a second lens.

Optical specifications of the objective optical system of the example 1 are as follows.

| maximum image height | 0.242 mm |
| angle of view | 116.8° |
| focal length | 0.263 mm |
| Fno | 3.529 |

These optical specifications are specifications envisaging an application to an objective optical system of mainly an extremely thin bronchial endoscope.

A flare stop FS and a filter plate FP are disposed between the planoconcave negative lens L1 and the planoconvex positive lens L2. An optical plate OP and an optical plate IPP are disposed on an image side of the planoconvex positive lens L2. An image pickup surface IS is disposed at an image position of the objective optical system.

The planoconcave negative lens L1 is a lens in which an outer diameter Φ is 0.86 mm, an axial lens thickness is 0.2 mm, and a radius of curvature of an image-side surface is 0.3 mm.

Sapphire is used for the material of the planoconcave negative lens L1 envisaging that the lens is to be soldered to the frame. The refractive index of sapphire is 1.7682 and Abbe number for sapphire is 71.79. When the refractive index of sapphire and a refractive index of an optical glass having substantially same refractive index are compared, sapphire has low dispersion. Therefore, sapphire is suitable as a material of the planoconcave negative lens L1.

The flare stop FS is formed of a thin plate in which a thickness is 0.03 mm. An opening is formed in this thin plate. A diameter of the opening is 0.32 mm. The flare stop FS cuts off unnecessary light incident from outside of a field of view and inducing flare.

For a material of the filter plate FP, a color correction filter is used. A thickness of the color correction filter is 0.3 mm.

The color correction filter has a characteristic of absorbing light of a near infrared wavelength region. Furthermore, on both surfaces of the filter plate FP, a multilayer film which reflects Nd:YAG (neodymium:yttrium aluminum garnet) laser is coated. Accordingly, it is possible to prevent an occurrence of image saturation at the time of treating mucous membrane.

The aperture stop AS is formed of a thin plate in which a thickness is 0.01 mm. An opening is formed in this thin plate. A diameter Φ of the opening is 0.14 mm.

In a case in which the thickness is excessively large with respect to a size of the opening, light is reflected and scattered at an edge of the opening. There is a possibility that the reflected light and the scattered light cause flare. In such manner, when the thickness is excessively large with respect to the size of the opening, the flare becomes a problem. In the objective optical system of the example 1, the opening of the aperture stop AS being extremely small, the thickness is made thin.

In the optical design, the thickness of the aperture stop AS is zero. The aperture stop AS is disposed at a position where a height of an axial marginal light ray is high and a diameter of an axial light beam is determined, or in other words, at a position on the planoconvex positive lens L2 side.

The planoconvex positive lens L2 is a lens in which an outer diameter is 0.52 mm and an axial lens thickness is 0.45 mm. In the planoconvex positive lens L2, an edge thickness of 0.3 mm is secured taking into consideration the workability and assemblability of the lens.

When the edge thickness is excessively small, it becomes difficult to hold a lens by tweezers or a fixture. As a result, workability at the time of manufacturing a lens and assembling lenses is degraded. Moreover, a margin to adhere at the time of fixing the planoconvex positive lens L2 to the lens frame is also necessary. For the abovementioned reasons, for the planoconvex positive lens L2, it is necessary to secure an edge thickness of about 0.3 mm.

In the example 1, an aspheric surface is used for an image-side surface of the second lens. More specifically, in the planoconvex positive lens L2, the image-side surface is an aspheric surface having a shape such that a curvature becomes small at a periphery. An axial radius of curvature of the aspheric surface is 0.2718 mm.

The planoconvex positive lens L2 is envisaged to be manufactured by glass molding. Therefore, L-LAL12 (manufactured by Ohara Corporation) which is a low transition point glass is used for the material of the planoconvex positive lens L2.

The transition point for L-LAL12 is 562° C. This temperature is a comparatively low temperature as an optical glass having a high refractive index and low dispersion. The refractive index of L-LAL12 is 1.6779, and Abbe number for L-LAL12 is 54.89. As L-LAL12 has a favorable balance of the refractive index and dispersion, it is one of suitable glasses for the planoconvex positive lens L2.

The optical plate OP is a circular plate in which a diameter is 0.62 mm. The optical plate OP is cemented to the optical plate IPP by an optical adhesive. Before cementing the optical plate IPP, centering by the optical plate OP and the optical plate IPP is carried out. When a central axis of the optical plate IPP and a center of the image pickup surface IS are made to coincide, by carrying out centering adjustment by the optical plate OP and the optical plate IPP, it is possible to make the center of the image pickup surface IS of the imager and the central shaft of the optical plate OP coincide.

When the centering adjustment is finished, the optical adhesive is let to be cured. For the optical adhesive, it is desirable to use a UV curing adhesive having a favorable workability. Therefore, glass having a high UV transmittance is used for the material of the optical plate OP. Generally, for a glass having a low refractive index and low dispersion, the UV transmittance is high. Therefore, the glass having a low refractive index and low dispersion is used for the optical plate OP.

The objective optical system includes a plurality of optical members. The optical members have variation in thickness due to manufacturing error. Therefore, even when each optical member is disposed according to a design value, the focusing position differs for each objective optical system. For such reason, the focus adjustment becomes necessary for each objective optical system.

It is possible to use an air space between the planoconvex positive lens L2 and the optical plate OP can be used for the focus adjustment. In the focus adjustment, by changing a distance between the planoconvex positive lens L2 and the optical plate OP, a fluctuation in the focus is absorbed. In the focus adjustment, an adjustment range not smaller than ±0.05 is necessary. Therefore, the focus adjustment distance is necessary at least 0.1 mm or more.

When the distance between the planoconvex positive lens L2 and the optical plate OP is excessively small, there is a risk of the planoconvex positive lens L2 and the optical plate OP hitting each other. In the objective optical system of the example 1, the air space between the planoconvex positive lens L2 and the optical plate OP is 0.279 mm. Therefore, a space necessary for the focus adjustment is secured adequately.

As mentioned above, in the objective optical system of the present embodiment, the longitudinal chromatic aberration is further improved as compared to that in the conventional objective optical system which includes two lenses. The improvement in the longitudinal chromatic aberration will be described below.

For evaluation of the longitudinal chromatic aberration, a longitudinal chromatic aberration evaluation value VLCA is used. Moreover, for comparison with the examples, examples 1 to 5 of Japanese Patent Application Laid-open Publication No. 2009-288682 (hereinafter, referred to as 'comparison examples 1 to 5') will be used.

The longitudinal chromatic aberration evaluation value VLCA is expressed by the following expression.

$$VLCA = \Delta LCAgd/f$$

where, $\Delta LCAgd$ denotes an amount of longitudinal chromatic aberration for a g-line when the d-line is a reference, and f denotes a focal length of the objective optical system.

The objective optical system of the present embodiment is envisaged to be used not only for white light observation but also for the narrow-band light observation. In the narrow-band light observation, a wavelength region on a short wavelength side out of a wavelength region of visible light is used. Therefore, in evaluation of the longitudinal chromatic aberration, an amount of axial aberration for the g-line is used. Moreover, in order to eliminate an effect due to a difference in the focal length, normalization by the focal length is carried out.

The smaller the absolute value of VLCA, the smaller is the longitudinal chromatic aberration. Therefore, it is desirable that the absolute value of VLCA be small.

A value of VLCA in the example 1 and values of VLCA in the comparison examples 1 to 5 are shown below.

|  | VLCA |
| --- | --- |
| example 1 | −6.6% |
| comparison example 1 | −11.9% |
| comparison example 2 | −11.0% |
| comparison example 3 | −12.1% |
| comparison example 4 | −11.0% |
| comparison example 5 | −10.8% |

The value of VLCA in the example 1 is smaller than the values of VLCA in the comparison examples 1 to 5. Therefore, the longitudinal chromatic aberration in the example 1 is improved more than the longitudinal chromatic aberration in the comparison examples 1 to 5.

The reason for the improvement is that a material which satisfies conditional expression (5) is used for the planoconvex positive lens L2. In such manner, the selection of material of the planoconvex positive lens L2 is a dominant factor for the improvement in the longitudinal chromatic aberration. The improvement in the longitudinal chromatic aberration can be said to be due to an effect of the material selection based on conditional expression (5).

Example 2

An objective optical system according to an example 2 will be described below. The objective optical system of the example 2 includes in order from an object side, a planoconcave negative lens L1 having a flat surface directed toward the object side, an aperture stop AS, and a planoconvex positive lens L2 having a flat surface directed toward the object side. The aperture stop AS is positioned on an object-side surface of the planoconvex positive lens L2. The planoconcave negative lens L1 is a first lens and the planoconvex positive lens L2 is a second lens.

Optical specifications of the objective optical system of the example 2 are as follows.

| maximum image height | 0.242 mm |
| --- | --- |
| angle of view | 116.8° |
| focal length | 0.266 mm |
| Fno | 3.562 |

These optical specifications are specifications envisaging an application to an objective optical system of mainly an extremely thin bronchial endoscope.

In the objective optical system of the example 2, the maximum image height and the angle of view are same as in the objective optical system of the example 1. Moreover, the planoconcave negative lens L1 of the example 2 is same as the planoconcave negative lens L1 of the example 1.

The main point that differs from the objective optical system of the example 1 is the refractive index of the material of the second lens. In the example 2, the material of the second lens is changed to a material having even higher refractive index.

In the planoconvex positive lens L2, an outer diameter is 0.52 mm, and an edge thickness is 0.3 mm. In such manner, the outer diameter and the edge thickness are same as the planoconvex positive lens L2 of the example 1. However, an axial lens thickness is 0.43 mm which is thinner than the axial lens thickness of the planoconvex lens L2 of the example 1.

In the planoconvex positive lens L2, an image-side surface is an aspheric surface having a shape such that a curvature becomes smaller at a periphery. An axial radius of curvature of the aspheric surface is 0.3006 mm.

The planoconvex positive lens L2 is envisaged to be manufactured by glass molding. In the example 2, L-LAH91 (manufactured by Ohara Corporation) is used for the material of the planoconvex positive lens L2. This point differs from that in the example 1.

The transition point for L-LAH91 is 611° C. This temperature is a comparatively low temperature as an optical glass having a high refractive index and low dispersion. Although L-LAH91 is a glass having a low transition temperature, the refractive index thereof is higher than the refractive index of L-LAL12 of the example 1. The refractive index of L-LAH91 is 1.7645, and Abbe number for L-LAH91 is 49.09. As L-LAH91 has a favorable balance of the refractive index and dispersion, too, it is one of the suitable glasses for the planoconvex positive lens L2.

In the planoconvex positive lens L2 of the example 2, the axial curvature of the aspheric surface is smaller than the axial curvature of the aspheric surface of the planoconvex positive lens L2 of the example 1. In such manner, by making the refractive index of the material of the planoconvex positive lens L2 high, it is possible to make the axial curvature of the aspheric surface small. By doing so, it is possible to improve the workability of a mold for glass molding more than in the example 1.

In the objective optical system of the example 2, an air space between the planoconvex positive lens L2 and an optical plate OP is 0.268 mm. Therefore, a space necessary for focus adjustment is secured adequately.

The improvement in the longitudinal chromatic aberration will be described below. A value of VLCA in the example 2 and values of VLCA in the comparison examples 1 to 5 are shown below.

|  | VLCA |
| --- | --- |
| example 2 | −7.5% |
| comparison example 1 | −11.9% |
| comparison example 2 | −11.0% |
| comparison example 3 | −12.1% |
| comparison example 4 | −11.0% |
| comparison example 5 | −10.8% |

The value of VLCA in the example 2 is smaller than the values of VLCA in the comparison examples 1 to 5. Therefore, the longitudinal chromatic aberration in the example 2 is improved more than the longitudinal chromatic aberration in the comparison examples 1 to 5.

The value of VLCA in the example 2 is −7.5% and the value of VLCA in the example 1 is −6.6%. When absolute values are compared, the value of VLCA in the example 2 is larger than the value of VLCA in the example 1.

Thus, in the example 2, the longitudinal chromatic aberration is deteriorated slightly as compared to the longitudinal chromatic aberration in the example 1. The reason for deterioration is that the dispersion of the material of the planoconvex positive lens L2 has become large.

Example 3

An objective optical system according to an example 3 will be described below. The objective optical system of the example 3 includes in order from an object side, a planoconcave negative lens L1 having a flat surface directed toward the object side, an aperture stop AS, and a planoconvex positive lens L2 having a flat surface directed toward the object side. The aperture stop AS is positioned on an object-side surface of the planoconvex positive lens L2. The planoconcave negative lens L1 is a first lens and the planoconvex positive lens L2 is a second lens.

Optical specifications of the objective optical system of the example 3 are as follows.

| maximum image height | 0.242 mm, |
| angle of view | 116.8° |
| focal length | 0.262 mm |
| Fno | 3.514 |

These optical specifications are specifications envisaging an application to an objective optical system of mainly an extremely thin bronchial endoscope.

In the objective optical system of the example 3, the maximum image height and the angle of view are same as in the objective optical system of the example 1. Moreover, the planoconcave negative lens L1 of the example 3 is same as the planoconcave negative lens L1 of the example 1.

The main point that differs from the objective optical system of the example 1 is Abbe number of a material of the second lens. In the example 3, the material of the second lens is changed to a material having even lower dispersion.

In the planoconvex positive lens L2, an outer diameter is 0.52 mm. Thus, the outer diameter is same as the planoconvex positive lens L2 of the example 1 and the planoconvex positive lens L2 of the example 2. However, an axial lens thickness is 0.46 mm which is thicker than the axial lens thickness of the planoconvex positive lens L2 of the example 1. Moreover, an edge thickness of 0.31 mm is secured.

In the planoconvex positive lens L2, an image-side surface is an aspheric surface having a shape such that a curvature becomes smaller at a periphery. An axial radius of curvature of the aspheric surface is 0.2634 mm.

The planoconvex positive lens L2 is envisaged to be manufactured by glass molding. In the example 3, S-LAL7 (manufacture by Ohara Corporation) is used for the material of the planoconvex positive lens L2. This point differs from that in the example 1.

The transition point for S-LAL7 is 617° C. This temperature is a comparatively low temperature as an optical glass having a high refractive index and low dispersion. Although S-LAL7 is a glass having a low transition temperature, the dispersion thereof is lower than the dispersion of L-LAL12 of the example 1. The refractive index of S-LAL7 is 1.6516, and Abbe number for S-LAL7 is 58.55. As S-LAL7 has a favorable balance of the refractive index and dispersion, too, it is one of the suitable glasses for the planoconvex positive lens L2.

In the objective optical system of the example 3, an air space between the planoconvex positive lens L2 and the optical plate OP is 0.283 mm. Therefore, a space necessary for focus adjustment is secured adequately.

The improvement in the longitudinal chromatic aberration will be described below. A value of VLCA in the example 3 and values of VLCA in the comparison examples 1 to 5 are shown below.

| | VLCA |
|---|---|
| example 3 | −6.1% |
| comparison example 1 | −11.9% |
| comparison example 2 | −11.0% |

-continued

| | VLCA |
|---|---|
| comparison example 3 | −12.1% |
| comparison example 4 | −11.0% |
| comparison example 5 | −10.8% |

The value of VLCA in the example 3 is smaller than the values of VLCA in the comparison examples 1 to 5. Therefore, the longitudinal chromatic aberration in the example 3 is improved more than the longitudinal chromatic aberration in the comparison examples 1 to 5.

The value of VLCA in the example 3 is −6.1% and the value of VLCA in the example 1 is −6.6%. When absolute values are compared, the value of VLCA in the example 3 is smaller than the value of VLCA in the example 1.

Thus, in the example 3, the longitudinal chromatic aberration is improved as compared to the longitudinal chromatic aberration in the example 1. The reason for improvement is that the dispersion of the material of the planoconvex positive lens L2 has become small.

Example 4

An objective optical system according to an example 4 will be described below. The objective optical system of the example 4 includes in order from an object side, a planoconcave negative lens L1 having a flat surface directed toward the object side, an aperture stop AS, and a planoconvex positive lens L2 having a flat surface directed toward the object side. The aperture stop AS is positioned on an object-side surface of the planoconvex positive lens L2. The planoconcave negative lens L1 is a first lens and the planoconvex positive lens L2 is a second lens.

Optical specifications of the objective optical system of the example 4 are as follows.

| maximum image height | 0.242 mm |
| angle of view | 116.8° |
| focal length | 0.265 mm |
| Fno | 3.529 |

These optical specifications are specifications envisaging an application to an objective optical system of mainly an extremely thin bronchial endoscope.

In the objective optical system of the example 4, the maximum image height and the angle of view are same as in the objective optical system of the example 1.

The main point that differs from the objective optical system of the example 1 is the refractive index of a material of the first lens. In the example 4, the material of the first lens is changed to a material having even higher refractive index.

In the planoconcave negative lens L1, an outer diameter is 0.86 mm, an axial lens thickness is 0.2 mm, and a radius of curvature of an image-side surface is 0.35 mm. In such manner, the outer diameter, the axial lens thickness, and the radius of curvature of the image-side surface are same as the planoconcave negative lens L1 of the example 1. However, the material of the planoconcave negative lens L1 is not sapphire, and lanthanum high refractive index glass is used for the material of the planoconcave negative lens L1. Lanthanum high refractive index glass is a type of optical glass.

The refractive index of the material of the planoconcave negative lens L1 is 1.883 and Abbe number for the material of the planoconcave negative lens L1 is 40.76. A glass code for this material is 883408. The material indicated by this number being sold as a product by manufacturers of optical glasses, it is easy to procure this material.

The dispersion of the material of the planoconcave negative lens L1 is higher than the dispersion of sapphire. Moreover, the refractive index of the material of the planoconcave negative lens L1 is higher than the refractive index of sapphire.

Since Sapphire is too hard, it is difficult to grind, and has disadvantage for workability. Whereas, the lanthanum high refractive index glass has a workability more favorable than the workability of sapphire.

Furthermore, by making the refractive index of the material of the planoconcave negative lens L1 high, it is possible to make large the radius of curvature of the image-side surface of the planoconcave negative lens L1. As a result, it is possible to improve workability of grinding the concave surface.

As a fixation of the planoconcave negative lens L1 to a frame, a fixation by soldering or a fixation by gluing can be used. The fixation by soldering has a higher airtightness and durability after fixing to the frame as compared to the fixation by gluing. However, in the fixation by soldering, the planoconcave negative lens L1 is required to have a high strength with respect to expansion and contraction.

The strength of the lanthanum high refractive index glass with respect to expansion and contraction is lower than that of sapphire. However, the workability of the lanthanum high refractive index glass is superior to that of sapphire. Therefore, in a case in which high airtightness and high durability is not required as in soldering, by fixing the lanthanum high refractive index glass to the frame by gluing, it is possible to reduce a component cost. Thus, the use of the lanthanum high refractive index glass is useful for the reduction of the component cost.

An outer diameter of the planoconvex lens L2 is 0.52 mm, and an axial thickness and the material of the planoconvex positive lens is same as the planoconvex positive lens L2 of the example 1. However, due to the change of the planoconcave negative lens L1, a shape of the image-side surface is changed slightly.

The improvement in the longitudinal chromatic aberration will be described below. A value of VLCA in the example 4 and values of VLCA in the comparison examples 1 to 5 are shown below.

|  | VLCA |
| --- | --- |
| example 4 | −5.8% |
| comparison example 1 | −11.9% |
| comparison example 2 | −11.0% |
| comparison example 3 | −12.1% |
| comparison example 4 | −11.0% |
| comparison example 5 | −10.8% |

The value of VLCA in the example 4 is smaller than the values of VLCA in the comparison examples 1 to 5. Therefore, the longitudinal chromatic aberration in the example 4 is improved more than the longitudinal chromatic aberration in the comparison examples 1 to 5.

The value of VLCA in the example 4 is −5.8% and the value of VLCA in the example 1 is −6.6%. When absolute values are compared, the value of VLCA in the example 4 is smaller than the value of VLCA in the example 1.

Thus, in the example 4, the longitudinal chromatic aberration is improved as compared to the longitudinal chromatic aberration in the example 1. The reason for improvement is that the dispersion of the material of the planoconcave negative lens L1 becomes large.

However, in the example 4, Abbe number for the material of the planoconcave negative lens L1 is made smaller by approximately 31 than that in the example 1. In spite of that, the extent of improvement in the longitudinal chromatic aberration is small. The degree of contribution of Abbe number to the improvement in the longitudinal chromatic aberration is such that contribution of Abbe number for the material of the planoconvex positive lens L2 is higher than contribution of the Abbe number for the material of the planoconcave negative lens L1.

Example 5

An objective optical system according to an example 5 will be described below. The objective optical system of the example 5 includes in order from an object side, a planoconcave negative lens L1 having a flat surface directed toward the object side, an aperture stop AS, and a biconvex positive lens L2. The aperture stop AS is positioned on the object side of the biconvex positive lens L2. The planoconcave negative lens L1 is a first lens and the biconvex positive lens L2 is a second lens.

Optical specifications of the objective optical system of the example 5 are as follows.

| | |
| --- | --- |
| maximum image height | 0.242 mm |
| angle of view | 116.8° |
| focal length | 0.261 mm |
| Fno | 3.508 |

These optical specifications are specifications envisaging an application to an objective optical system of mainly an extremely thin bronchial endoscope.

In the objective optical system of the example 5, the maximum image height and the angle of view are same as in the objective optical system of the example 1. Moreover, the planoconcave negative lens L1 of the example 5 is same as the planoconcave negative lens L1 of the example 1. A combination of the materials of the two lenses is also same as in the example 1.

The main point that differs from the objective optical system of the example 1 is a shape of the second lens. In the example 5, a shape of the second lens is changed from a planoconvex shape to a biconvex shape. By this change, the longitudinal chromatic aberration, the spherical aberration, and the coma are improved.

In the biconvex positive lens L2, an outer diameter is 0.52 mm. Thus, the outer diameter is same as the planoconvex positive lens L2 of the example 1. Moreover, the material of the biconvex positive lens L2 is also same as in the example 1. However, the shape of the biconvex positive lens L2 differs between the example 5 and the example 1.

In the biconvex positive lens L2 of the example 5, not only that an image-side surface is a surface which is convex toward an image side but also an object-side surface is a surface which is convex toward the object side. Moreover, the object-side surface of the biconvex positive lens L2 is a spherical surface and the image-side surface of the biconvex positive lens L2 is an aspheric surface.

The biconvex positive lens L2 is envisaged to be manufactured by glass molding.

The aperture stop AS being a thin plate, it is preferable to avoid holding singularly. In the biconvex positive lens L2 of the example 5, a flange is formed on the object-side surface.

The flange is formed at an outer side of an effective aperture of the object-side surface. The flange has a flat portion orthogonal to an optical axis. By bringing the aperture stop AS in contact with the flat portion, it is possible to hold the aperture stop AS by the biconvex positive lens L2.

Moreover, when the aperture stop AS is brought in contact with the flange, the aperture stop AS and the object-side surface should not come in contact. For this, it is necessary to provide a space between the aperture stop AS and the object-side surface. In the biconvex positive lens L2, the aperture stop AS is to be positioned on the object side of an apex of the object-side surface.

When the flange is formed on an outer peripheral side of the biconvex positive lens L2, it is possible to secure a stable lens posture by simple assembly of just bringing the aperture stop AS in contact with the flange similarly as in the case of the planoconvex positive lens.

In a case in which there is no flange on the object-side surface, either an optical quality or a manufacturability and cost are degraded. For instance, in a case of bringing a convex surface near a center in contact with an opening portion of the aperture stop AS, tilt of the biconvex positive lens L2 susceptible occurs. When the tilt o the biconvex positive lens L2 occurs, the optical quality is degraded. Moreover, in a structure in which a spacer is interposed as a separate component between the aperture stop and the biconvex positive lens L2, an assemblability and cost are affected adversely due to an addition of an extremely small spacer.

When a flange is formed on an outer peripheral side of the biconvex positive lens L2, it is possible to make the axial lens thickness thin in a state of an edge thickness of the biconvex positive lens secured. In addition to an effect by making the lens shape the biconvex shape, it is possible to shorten the overall length of the optical system.

In the biconvex positive lens L2 of the example 5, an axial lens thickness is 0.4 mm which is thinner by 0.05 mm than the axial lens thickness of the planoconvex positive lens L2 of the example 1, while securing the edge thickness of 0.31 mm which is almost same as the edge thickness of the planoconvex positive lens L2 of the example 1.

By making the lens shape biconvex shape, it is possible to let a part of the refractive power of the image-side surface be shared by the object-side surface. Moreover, it is possible to position a principal point of the biconvex positive lens L2 on the object side of the image-side surface. As a result, a favorable design is possible even without making the back focus longer than necessary.

With the effect described above, in the objective optical system of the example 5, an overall length of the optical system is shortened to 1.816 mm, while the overall length of the optical system of the example 1 is 1.969 mm.

In the biconvex positive lens L2, the image-side surface is an aspheric surface having a shape such that the curvature becomes small at the periphery. An axial radius of curvature of the aspheric surface is 0.3096 mm.

In the biconvex positive lens L2, an axial curvature of the aspheric surface is smaller than the axial curvature of the aspheric surface of the planoconvex positive lens L2 of the example 1. By dividing the refractive power of the biconvex positive lens between the object-side surface and the image-side surface, it is possible to weaken the refractive power of the image-side surface. By making the curvature of the image-side surface small, it is possible to improve workability of the mold for glass molding used for forming the image-side surface.

In the objective optical system of the example 5, an air space between the biconvex positive lens L2 and an optical plate OP is 0.156 mm. This space is shorter than the space in the example 1. However, since the space of 1 mm or more could be secured, the space necessary for the focus adjustment is secured.

The improvement in the longitudinal chromatic aberration will be described below. A value of VLCA in the example 5 and values of VLCA in the comparison examples 1 to 5 are shown below.

|  | VLCA |
| --- | --- |
| example 5 | −5.1% |
| comparison example 1 | −11.9% |
| comparison example 2 | −11.0% |
| comparison example 3 | −12.1% |
| comparison example 4 | −11.0% |
| comparison example 5 | −10.8% |

The value of VLCA in the example 5 is smaller than the values of VLCA in the comparison examples 1 to 5. Therefore, the longitudinal chromatic aberration in the example 5 is improved more than the longitudinal chromatic aberration in the comparison examples 1 to 5.

The value of VLCA in the example 5 is −5.1% and the value of VLCA in the example 1 is −6.6%. When absolute values are compared, the value of VLCA in the example 5 is smaller than the value of VLCA in the example 1.

Thus, in the example 5, the longitudinal chromatic aberration is improved as compared to the longitudinal chromatic aberration in the example 1. The reason for the improvement is that by making the lens shape biconvex shape, it was possible to shorten the focal length of the biconvex positive lens L2.

In the example 5, the focal length of the biconvex positive lens L2 is 0.379 mm and in the example 1 the focal length of the planoconvex positive lens L2 is 0.401 mm. The longitudinal chromatic aberration is prone to improve in proportion to the focal length. Therefore, when it possible to shorten the focal length even with the same material of the lens, it is possible to improve the longitudinal chromatic aberration.

The improvement in the spherical aberration will be described below. For evaluation of the spherical aberration, a spherical aberration evaluation value VSA is used. The spherical aberration evaluation value VSA is expressed by the following expression.

$$VSa = \Delta SAd/f$$

where,

ΔSAd denotes an amount of spherical aberration for a d-line of a marginal light ray, and F denotes a focal length of the objective optical system.

The smaller the absolute value of VSA, the smaller is the spherical aberration. Therefore, it is desirable that the absolute value of VSA be small.

The value of VSA in the example 5 and the value of VSA in the example 1 are shown below

|  | VSA |
| --- | --- |
| example 5 | −10.2% |
| example 1 | −25.6% |

The value of VSA in the example 5 is-10.2%, and the value of VSA in the example 1 is −25.6%. When absolute values are compared, the value of VSA in the example 5 becomes significantly smaller than the value of VSA in the example 1.

Thus, in the example 5, the spherical aberration is improved more than the spherical aberration in the example 1. The reason for the improvement is that by making the shape of the lens biconvex shape, the refractive power of the biconvex positive lens L2 is divided between the two lens surfaces.

The improvement in the coma will be described below. For evaluation of the coma, a coma evaluation value VCMA is used. The coma evaluation value VCMA is expressed by the following expression.

$$VCMA = \Delta CMA/f$$

where, $\Delta CMA$ denotes a distance in an optical axial direction between two predetermined points, and f denotes the focal length of the objective optical system, and here the two predetermined points are a point of intersection of a principal light ray and an upper subordinate light ray and a point of intersection of the principal light ray and a lower subordinate light ray.

The smaller the absolute value of VCMA, the smaller is the coma. Therefore, it is desirable that the absolute value of VCMA be small.

The value of VCMA in the example 5 and the value of VCMA in the example 1 are shown below.

|  | VCMA |
| --- | --- |
| Example 5 | −33.8% |
| Example 1 | −59.4% |

The value of VCMA in the example 5 is −33.8%, and the value of VCMA in the example 1 is −59.4%. When absolute values are compared, the value of VCMA in the example 5 becomes significantly smaller than the value VCMA in the example 1.

Thus, in the example 5, the coma is improved more than in the example 1. The reason for the improvement is that by making the shape of the lens biconvex shape, the refractive power of the biconvex positive lens L2 is divided between the two lens surfaces.

Example 6

An objective optical system according to an example 6 will be described below. The objective optical system of the example 6 includes in order from an object side, a planoconcave negative lens L1 having a flat surface directed toward the object side, an aperture stop AS, and a biconvex positive lens L2. The aperture stop AS is positioned on the object side of the biconvex positive lens L2. The planoconcave negative lens L1 is a first lens and the biconvex positive lens L2 is a second lens.

Optical specifications of the objective optical system of the example 6 are as follows.

| maximum image height | 0.242 mm |
| angle of view | 116.8° |
| focal length | 0.262 mm |
| Fno | 3.511 |

These optical specifications are specifications envisaging an application to an objective optical system of mainly an extremely thin bronchial endoscope.

In the objective optical system of the example 6, the maximum image height and the angle of view are same as in the objective optical system of the example 5. Moreover, the planoconcave negative lens L1 in the example 6 is same as the planoconcave negative lens L1 in the example 5. A combination of the materials of the two lenses is also same as in the example 5.

The main point that differs from the objective optical system of the example 5 is the number of aspheric surfaces used in the second lens. In the example 6, an aspheric surface is used for both surfaces of the second lens. By this change, the spherical aberration and the coma are improved further.

In the biconvex positive lens L2, an outer diameter is 0.52 mm, an axial lens thickness is 0.4 mm, an edge thickness of lens is 0.31 mm, and an overall length of the optical system is 1.816 mm. Thus, the outer diameter, the axial lens thickness, and the overall length of the optical system are same as the biconvex positive lens of the example 5. Moreover, the material of the biconvex positive lens L2 is also same as the biconvex positive lens of the example 5. However, the number of aspheric surfaces differ in the example 6 and the example 5.

In the biconvex positive lens L2 of the example 6, not only that an image-side surface is an aspheric surface, but also an object-side surface is an aspheric surface.

The biconvex positive lens L2 is envisaged to be manufactured by glass molding. Moreover, similarly as in the biconvex positive lens L2 of the example 5, a flange is formed on an outer peripheral side of the object-side surface.

In the biconvex positive lens L2, both the image-side surface and the object-side surface are aspheric surfaces having a shape such that a curvature becomes small at a periphery. The aspheric surface on the image-side surface contributes mainly to correction of the astigmatism. Therefore, by making only the image-side surface an aspheric surface, some spherical aberration and some coma sill remain.

In the biconvex positive lens L2, by making the object-side surface a surface which is convex toward the object side, and further making an aspheric surface, the degree of freedom of correction is improved. By doing so, it is possible to correct favorably a residual spherical aberration and a residual coma.

The object-side surface is positioned near the aperture stop AS. Therefore, making the object-side surface an aspheric surface does not affect almost on the astigmatism. Therefore, the aspheric surface of the object-side surface contributes to correct the spherical aberration and the coma without causing the astigmatism to be deteriorated.

The improvement in the spherical aberration will be described below. A value of VSA in the example 6 and the value of VSA in the example 5 are shown below.

|  | VSA |
| --- | --- |
| Example 6 | 0.0% |
| Example 5 | −10.2% |

The value of VSA in the example 6 is 0%, and the value of VSA in the example 5 is −10.2%. In the example 6, the spherical aberration could be corrected completely.

The improvement in the coma will be described below. A value of VCMA in the example 6 and the value of VCMA in the example 5 are shown below.

|  | VCMA |
| --- | --- |
| Example 6 | −14.7% |
| Example 5 | −33.8% |

The value of VCMA in the example 6 is −14.7% and the value of VCMA in the example 5 is −33.8%. When absolute values are compared, the value of VCMA in the example 6 is significantly smaller than the value of VCMA in the example 5.

Thus, in the example 6, the coma is improved more than in the example 5. The reason for the improvement is that the object-side surface was made an aspheric surface.

The longitudinal chromatic aberration is not affected of making the object-side surface an aspheric surface. The value of VLCA in the example 6 is −5.1%. This is same as the value of VLCA in the example 5.

Example 7

An objective optical system according to an example 7 will be described below. The objective optical system of the example 7 includes in order from an object side, a planoconcave negative lens L1 having a flat surface directed toward the object side, an aperture stop AS, and a positive meniscus lens L2 having a convex surface directed toward an image side. The aperture stop AS is positioned on the object side of the positive meniscus lens L2. The planoconcave negative lens L1 is a first lens and the positive meniscus lens L2 is a second lens.

Optical specifications of the objective optical system of the example 7 are as follows.

| maximum image height | 0.242 mm |
| --- | --- |
| angle of view | 116.8° |
| focal length | 0.264 mm |
| Fno | 3.533 |

These optical specifications are specifications envisaging an application to an objective optical system of mainly an extremely thin bronchial endoscope.

In the objective optical system of the example 7, the maximum image height and the angle of view are same as in the objective optical system of the example 5. Moreover, the planoconcave negative lens L1 in the example 7 is same as the planoconcave negative lens L1 in the example 5.

The main point that differs from the objective optical system of the example 5 is a shape of the second lens and the number of aspheric surfaces used in the second lens. In the example 7, the shape of the second lens is changed from a biconvex shape to a meniscus shape, and an aspheric surface is used for both surfaces of the second lens. By these changes, the spherical aberration and the coma are improved further.

In the positive meniscus lens L2, an outer diameter is 0.52 mm. Thus, the outer diameter is same as the planoconvex positive lens L2 of the example 1. Moreover, an axial lens thickness of the positive meniscus lens L2 is 0.43 mm which is thinner by 0.02 mm than the axial lens thickness of the planoconvex positive lens L2, while securing an edge thickness of 0.31 mm which is almost same as the edge thickness of the planoconvex positive lens L2 of the example 1. However, the shape of the lens differs in the example 7 and the example 1.

In the positive meniscus lens L2 of the example 7, an aspheric surface is used for an object-side surface. While the object-side surface is a flat surface paraxially, taking into consideration an aspheric surface, the object-side surface is a surface which is concave toward the object side. An image-side surface being a surface which is convex toward an image side, in the example 7, the second lens can be deemed as a meniscus lens having a convex surface directed toward the image side.

The positive meniscus lens L2 is envisaged to be manufactured by glass molding.

A flat surface portion is formed on an outer peripheral side of the object-side surface of the positive meniscus lens L2. The flat surface portion is provided for bringing the aperture stop AS in contact, and is functionally same as the flange in the example 5 or the flange in the example 6.

However, the flange in the example 5 and the flange in the example 6 are formed to protrude from a convex surface. Consequently, a step is formed at a boundary portion of the convex surface and the flange. Whereas, in the example 7, the flat surface portion which becomes a flange, is on an extension of the object-side concave surface. Almost no step is formed at a boundary of the flat surface portion which becomes the flange, and the object-side concave surface.

From a view point of processing of a mold for the glass molding and an amount of deformation of glass, it is desirable that a step on the mold surface is small. When compared with the example 5 and the example 6, the shape of the object-side surface is suitable for glass molding.

In the positive meniscus lens L2, the image-side surface is an aspheric surface having a shape such that the curvature becomes small at the periphery. The aspheric surface of the image-side surface contributes mainly to the correction of the astigmatism. Therefore, by making only the image-side surface an aspheric surface, some spherical aberration and some coma sill remain.

By making the object-side surface of the positive meniscus lens L2 an aspheric surface, it is possible to improve the degree of freedom of correction. It is preferable to make the object-side surface an aspheric surface that can be expressed by only a fourth-order aspherical coefficient, and to impart a negative refractive power to a peripheral side. In this case, although the shape of the object-side surface becomes a concave surface, a center of curvature being zero, the paraxial refractive power is zero.

By making the object-side surface an aspheric surface that can be expressed only by the fourth-order aspherical coefficient, it is possible to impart an effect of a negative refractive power to the object-side surface. By the effect of the negative refractive power, it is possible to generate the spherical aberration and the coma prone to excessive correction in the positive meniscus lens L2.

Each of a residual spherical aberration and a residual coma is prone to be corrected inadequately. By making the object-side surface an aspheric surface, it is possible to correct the residual spherical aberration and the residual coma.

The object-side surface is positioned near the aperture stop AS. Therefore, making the object-side surface an aspheric surface does not affect almost on the astigmatism. Therefore, the aspheric surface of the object-side surface contributes to correct the spherical aberration and the coma without causing the astigmatism to be deteriorated.

The improvement in the spherical aberration will be described below. A value of VSA in the example 7 and the value of VSA in the example 5 are shown below.

|  | VSA |
|---|---|
| Example 7 | 0.0% |
| Example 5 | −10.2% |

The value of VSA in the example 7 is 0%, and the value of VSA in the example 5 is −10.2%. In the example 7, the spherical aberration could be corrected completely.

The improvement in the coma will be described below. A value of VCMA in the example 7 and the value of VCMA in the example 5 are shown below.

|  | VCMA |
|---|---|
| Example 7 | −19.2% |
| Example 5 | −33.8% |

The value of VCMA in the example 7 is −19.2% and the value of VCMA in the example 5 is −33.8%. When absolute values are compared, the value of VCMA in the example 7 is smaller than the value of VCMA in the example 5.

Thus, in the example 7, the coma is improved more than in the example 5. The reason for the improvement is that the object-side surface was made an aspheric surface.

The longitudinal chromatic aberration is not affected of making the object-side surface an aspheric surface. The value of VLCA in the example 7 is −6.7%. This is almost same as the value of VLCA in the example 1, and slightly smaller to the value of VLCA in the example 5.

Example 8

An objective optical system according to an example 8 will be described below. The objective optical system of the example 8 includes in order from an object side, a planoconcave negative lens L1 having a flat surface directed toward the object side, an aperture stop AS, and a biconvex positive lens L2. The aperture stop AS is positioned on an object-side surface of the biconvex positive lens L2. The planoconcave negative lens L1 is a first lens and the biconvex positive lens L2 is a second lens.

Optical specifications of the objective optical system of the example 8 are as follows.

| maximum image height | 0.242 mm |
|---|---|
| angle of view | 90° |
| focal length | 0.322 mm |
| Fno | 4.092 |

These optical specifications are optical specifications envisaging an application to an objective optical system of mainly an extremely thin renal ureteroscope.

In the objective optical system of the example 8, the maximum image height is same as in the objective optical system of the example 5. Moreover, the planoconcave negative lens L1 of the example 8 is same as the planoconcave negative lens L1 of the example 5. A combination of the materials of the two lenses is also same as in the example 5.

The main point that differs from the objective optical system of the example 5 is the angle of view. In the objective optical system of the example 8, the angle of view is narrowed to 90° with the objective optical system of the example 5 as a base.

In the planoconcave negative lens L1, an outer diameter is 0.8 mm. In the objective optical system of the example 8, the angle of view is narrower than the angle of view in the objective optical system of the example 5. In this case, a height of a light ray incident on the planoconcave negative lens L1 becomes low. Therefore, it is possible to make the outer diameter of the planoconcave negative lens L1 smaller than the outer diameter of the planoconcave negative lens L1 in the example 5.

In the example 8, a thickness of a filter plate FP is 0.45 mm. Thickness of the filter plate FP is increased to be thicker than the thickness of the filter plate FP in the example 5. By doing so, it is possible to improve an adaptability to treatment by laser.

In a renal ureteroscope, treatment for a stone and a tumor by laser is carried out frequently. In the treatment by laser, near infrared light is used. In this case, a color correction filter which absorbs the near infrared light is used for the filter plate FP.

The larger the thickness of the absorbing filter, the higher is the rate of absorption. By increasing the thickness of the filter plate FP, it is possible to make low a light intensity of laser light incident on an imager. As a result, it is possible to reduce further the risk of occurrence of image saturation.

In the biconvex positive lens L2, an outer diameter is 0.52 mm, an object-side surface is a spherical surface, and an image-side surface is an aspheric surface. Thus, the outer diameter, the shape of the object-side surface, and the shape of the image side surface are same as in the example 5.

In the biconvex positive lens L2 of the example 8, an axial lens thickness is 0.36 mm which is thinner by 0.04 mm than the axial lens thickness of the biconvex positive lens L2 in the example 5, while securing an edge thickness of 0.3 mm which is almost same as the edge thickness of the biconvex positive lens L2 of the example 5.

The reason why the axial thickens could be made thin with respect to the edge thickness is that the angle of view is narrow. By the angle of view becoming narrow, it is possible to make a refractive power at each surface of the biconvex positive lens L2 small. In this case, since a radius of curvature of each surface becomes large, it is possible to make a distance between surfaces small.

In the objective optical system of the example 8, an overall length of the optical system is extended to 2.132 mm while the overall length of the optical system in the example 5 is 1.816 mm. However, the overall length of the optical system in the example 8, in absolute terms, is adequately short.

Both of an axial radius of curvature of the object-side surface and an axial radius of curvature of the image-side surface have absolute values larger than those in the example 5. Therefore, there is no problem regarding the processing of mold for glass molding.

In the objective optical system of the example 8, an air space between the biconvex positive lens L2 and an optical plate OP is 0.362 mm. Therefore, a space necessary for focus adjustment is secured adequately.

The improvement in the longitudinal chromatic aberration will be described below. A value of VLCA in the example 8, the value of VLCA in the example 5, and the values of VLCA in the comparison examples 1 to 5 are shown below.

|  | VLCA |
| --- | --- |
| example 8 | −6.6% |
| example 5 | −5.1% |
| comparison example 1 | −11.9% |
| comparison example 2 | −11.0% |
| comparison example 3 | −12.1% |
| comparison example 4 | −11.0% |
| comparison example 5 | −10.8% |

The value of VLCA in the example 8 is smaller than the values of VLCA in the comparison examples 1 to 5. Therefore, the longitudinal chromatic aberration in the example 8 is improved more than the longitudinal chromatic aberration in the comparison examples 1 to 5.

The value of VLCA in the example 8 is −6.6% and the value of VLCA in the example 5 is −5.1%. When absolute values are compared, the value of VLCA in the example 8 is higher than the value of VLCA in the example 5.

Thus, in the example 8, the longitudinal chromatic aberration is deteriorated slightly more than the longitudinal chromatic aberration in the example 5. The reason for deterioration is that the focal length of the biconvex positive lens L2 has become long due to the angle of view being narrowed. The focal length of the biconvex positive lens L2 is 0.454 mm in the example 8 and is 0.379 mm in the example 5.

Example 9

An objective optical system according to an example 9 will be described below. The objective optical system of example 9 includes in order from an object side, a planoconcave negative lens 11 having a flat surface directed toward the object side, an aperture stop AS, and a biconvex positive lens L2. The aperture stop AS is positioned on the object side of the biconvex positive lens L2. The planoconcave negative lens L1 is a first lens and a biconvex positive lens L2 is the second lens.

Optical specifications of the objective optical system of the example 9 are shown below.

| maximum image height | 0.198 mm, |
| --- | --- |
| angle of view | 116.8° |
| focal length | 0.212 mm |
| Fno | 3.279 |

These optical specifications are specifications envisaging an application to an objective optical system of mainly an extremely thin bronchial endoscope.

In the objective optical system of the example 9, the angle of view is same as in the objective optical system of the example 5. A combination of the materials of the two lenses is also same as in the example 5.

The main point that differs from the objective optical system of the example 5 is the maximum image height. In the objective optical system of the example 9, with the objective optical system of the example 5 as a base, the maximum image height is reduced to 0.82 times, and a diameter of the optical system is made thin.

In the planoconcave negative lens L1, an outer diameter is 0.76 mm. This is 0.1 mm smaller than the outer diameter of the planoconcave negative lens L1 of the example 5. By the maximum image height becoming low, a height of a light ray at the planoconcave negative lens L1 is lowered. Consequently, the outer diameter becomes small.

In the planoconcave negative lens L1, an axial lens thickness, a concave depth, and a radius of curvature are reduced as compared to those in the example 5.

A thickness of a filter plate FP is 0.25 mm. The thickness of the filter plate FP is thinner than the thickness of the filter plate FP in the example 5. Accordingly, a height of a light ray at the planoconcave negative lens is lowered. When the thickness of the filter plate FP becomes thin, a light intensity of laser light incident on an imager becomes high. However, by increasing a density of the material, it is possible to make lower the light intensity of laser light incident on the imager. As a result, it is possible to reduce risk of occurrence of image saturation.

In the biconvex positive lens L2, an outer diameter is 0.45 mm, an edge thickness of lens is 0.31 mm, an object-side surface is a spherical surface, and an image-side surface is an aspheric surface. Thus, the outer diameter, the edge thickness of lens, the shape of the object-side surface, and the shape of the image-side surface are same as the biconvex positive lens L2 of the example 5. Moreover, a point that the biconvex positive lens L2 has a flange on an outer peripheral side of the object-side surface is same as in the example 5. However, the maximum image height differs in the example 9 and the example 5.

In the biconvex positive lens L2, an axial lens thickness is 0.39 mm. This is almost same as the axial lens thickness in the example 5.

In the objective optical system of the example 9, an overall length of the optical system is shortened to 1.6 mm, while the overall length of the optical system in the example 5 is 1.816 mm.

In the objective optical system of the example 9, an air space between the biconvex positive lens L2 and an optical plate OP is 0.1 mm. Therefore, the minimum space necessary for focus adjustment is secured.

The improvement in the longitudinal chromatic aberration will be described below. A value of VLCA in the example 9, the value of VLCA in the example 5, and the values of VLCA in the comparison examples 1 to 5 are shown below.

|  | VLCA |
| --- | --- |
| example 9 | −5.1% |
| example 5 | −5.1% |
| comparison example 1 | −11.9% |
| comparison example 2 | −11.0% |
| comparison example 3 | −12.1% |
| comparison example 4 | −11.0% |
| comparison example 5 | −10.8% |

The value of VLCA in the example 9 is smaller than the values of VLCA in the comparison examples 1 to 5. Therefore, the longitudinal chromatic aberration in the example 9 is improved more than the longitudinal chromatic aberration in the comparison examples 1 to 5.

The value of VLCA in the example 9 is −5.1% which is same as the value of VLCA in the example 5.

Example 10

An objective optical system according to an example 10 will be described below. The objective optical system of the example 10 includes in order from an object side, a planoconcave negative lens L1 having a flat surface directed toward the object side, an aperture stop AS, and a biconvex positive lens L2. The aperture stop AS is positioned on the object side of the biconvex positive lens L2. The planoconcave negative lens L1 is a first lens and the biconvex positive lens L2 is a second lens.

Optical specifications of the objective optical system of the example 10 are shown below.

| | |
|---|---|
| maximum image height | 0.198 mm, |
| angle of view | 90° |
| focal length | 0.265 mm |
| Fno | 3.789 |

These optical specifications are specifications envisaging an application to an objective optical system of mainly an extremely thin renal ureteroscope.

In the objective optical system of the example 10, the angle of view is same as in the objective optical system of the example 8. A combination of the materials of the two lenses is also same as in the example 8.

The main point that differs from the objective optical system of the example 8 is the maximum image height. In the objective optical system of the example 10, with the objective optical system of the example 8 as a base, the maximum image height is reduced to 0.82 times, and a diameter of the optical system is made even thinner. The maximum image height in the example 10 is same as the maximum image height in the example 9.

In the planoconcave negative lens L1, an outer diameter is 0.68 mm. This is 0.12 mm smaller than the outer diameter of the planoconcave negative lens of the example 8. By the maximum image height becoming low, a height of a light ray at the planoconcave negative lens L1 is lowered. Consequently, the outer diameter become small.

In the planoconcave negative lens L1, an axial lens thickness, a concave depth, and a radius of curvature are reduced as compared to those in the example 8.

A thickness of a filter plate FP is 0.25 mm. The thickness of the filter plate FP is thinner than the thickness of the filter plate FP in the example 8. Accordingly, a height of a light ray at the planoconcave negative lens L1 is lowered. When the thickness of the filter plate FP becomes thin, a light intensity of laser light incident on an imager becomes high. However, by increasing a density of the material, it is possible to make low the light intensity of laser light incident on the imager. As a result, it is possible to reduce risk of occurrence of image saturation.

In the biconvex positive lens L2, an object-side surface is a spherical surface and an image-side surface is an aspheric surface. Thus, the shape of the object-side surface and the shape of the image-side surface are same as the biconvex positive lens L2 of the example 8. Moreover, the point that the biconvex positive lens L2 has a flange at an outer peripheral side of the object-side convex surface is also same as in the example 8. However, in the example 10, the outer diameter is Φ 0.45 mm. The outer diameter is reduced to be smaller than the outer shape of the biconvex positive lens L2 in the example 8.

In the biconvex positive lens L2 of the example 10, an axial lens thickness is 0.37 mm which is almost same as the axial lens thickness of the biconvex positive lens L2 of the example 5, while securing an edge thickness of 0.3 mm which is almost same as the edge thickness of the biconvex positive lens L2 in the example 5.

In an objective optical system of the example 10, an overall length of the optical system is shortened to 1.685 mm, while the overall length of the optical system in the example 8 is 2.132 mm.

In the objective optical system of the example 10, an air space between the biconvex positive lens L2 and an optical plate OP is 0.205 mm. Therefore, a space necessary for focus adjustment is secured adequately.

The improvement in the longitudinal chromatic aberration will be described below. A value of VLCA in the example 10, the value of VLCA in the example 8, and values of VLCA in the comparison examples 1 to 5 are shown below.

| | VLCA |
|---|---|
| example 10 | −5.5% |
| example 8 | −6.5% |
| comparison example 1 | −11.9% |
| comparison example 2 | −11.0% |
| comparison example 3 | −12.1% |
| comparison example 4 | −11.0% |
| comparison example 5 | −10.8% |

The value of VLCA in the example 10 is smaller than the values of VLCA in the comparison examples 1 to 5. Therefore, the longitudinal chromatic aberration in the example 10 is improved more than the longitudinal chromatic aberration in the comparison examples 1 to 5.

The value of VLCA in the example 10 is −5.5% and the value of VLCA in the example 8 is −6.5%. When absolute values are compared, the value of VLCA in the example 10 is smaller than the value of VLCA in the example 8.

Thus, in the example 10, the longitudinal chromatic aberration is improved even further than in the example 8.

As shown in each example described above, according to the objective optical system of the present embodiment, it is possible to realize an objective optical system which is available for various angles of view and image heights, and which can be mounted in an extremely thin video scope.

However, in the objective optical system of the present embodiment, the lateral chromatic aberration remains substantially. The residual lateral chromatic aberration is to be corrected electrically. The electrical correction of the lateral chromatic aberration is carried out by an endoscope system. For this, the endoscope system of the present embodiment has an image processor. The electrical correction of the lateral chromatic aberration will be described below.

From the objective optical system of the example 1 to the objective optical system of the example 7 have the same maximum image height and angle of view. In the seven examples, an example in which aberrations other than the lateral chromatic aberration are corrected most favorably is the example 6. Therefore, the electrical correction of the lateral chromatic aberration will be described below by using the example 6 as a representative example. However, the electrical correction of the lateral chromatic aberration is not restricted to the example 6. Electrical correction of the lateral chromatic aberration is applicable to all the examples.

In the example 6, aberrations which occur monochromatically, or in other words, the spherical aberration, the astigmatism, and the coma are corrected favorably. Furthermore, it is possible to reduce also an occurrence of the longitudinal chromatic aberration. Except for a distortion which does not affect a point spread function, an aberration that lowers the contrast of an image is the lateral chromatic aberration only.

For evaluation of the lateral chromatic aberration, lateral chromatic aberration evaluation values VCAMB1, VCAMB2, VCAMR are to be used. Each of longitudinal chromatic aberration evaluation values VCAMB and VCAMR are expressed by the following expressions.

$$VCAMB1 = \Delta CAMB1G/IHmax$$

$$VCAMB2 = \Delta CAMB2G/IHmax$$

$$VCAMR = \Delta CAMRG/IHmax$$

where, $\Delta CAMB1G$ denotes a lateral chromatic aberration for a B-band 1 with reference to a G-band, $\Delta CAMB2G$ denotes a lateral chromatic aberration for a B-band 2 with reference to the G-band, $\Delta CAMRG$ denotes a lateral chromatic aberration for an R-band with reference to the G-band, and IHmax denotes the maximum image height.

An amount of the lateral chromatic aberration is an amount in a radial direction in an image plane. In evaluation of the lateral chromatic aberration at the time of white light observation, the B-band 1 is used as the B-band, and furthermore, the G-band and the R-band are used. A representative wavelength of the B-band 1 is 460 nm, a representative wavelength of the G-band is 540 nm, and a representative wavelength of the R-band is 620 nm. Furthermore, wavelength 540 nm of the G-band is a reference wavelength.

In evaluation of the lateral chromatic aberration at the time of narrow-band light observation, the B-band 2 is used as the B-band and furthermore, the G-band is used. A representative wavelength of the B-band 2 is 415 nm and a representative wavelength of the G-band is 540 nm. Furthermore, wavelength 540 nm of the G-band is the reference wavelength.

Figure 12:
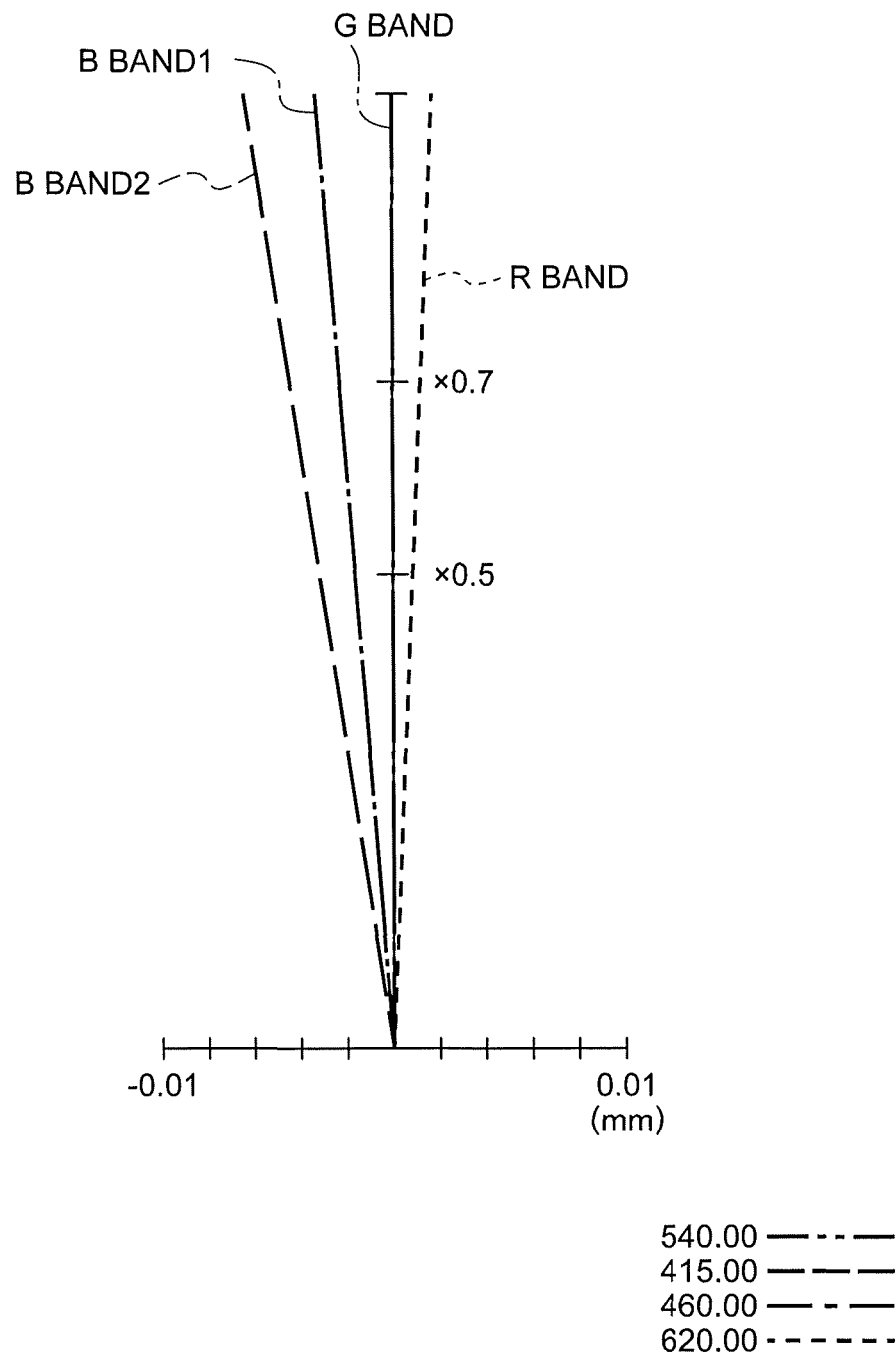
FIG. 12 is a diagram showing a lateral chromatic aberration of the objective optical system according to the example 6.

In FIG. 12, lateral chromatic aberration diagram of the objective optical system of the example 6 is shown. In the aberration diagram shown in FIG. 12, the reference wavelength is 540 nm. Each of the amount of lateral chromatic aberration at 415 nm, the amount of lateral chromatic aberration at 460 nm, and the amount of lateral chromatic aberration at 620 nm is almost linear with respect to the image height.

A value of VCAMB1, a value of VCAMB2, and a value of VCAMR in the example 6 are shown below.

|  | VCAMB1 | VCAMB2 | VCAMR |
| --- | --- | --- | --- |
| Example 6 | −1.35% | −2.6% | +0.81% |

Above-mentioned numerical values indicate that a position of an intersection point of an image plane and a principal light ray corresponding to the maximum image height differs for each of the B-band 1, the B-band 2, the G-band, and the R-band. An intersection point of the principal light ray for the B-band 1 is PB1, an intersection point of the principal light ray for the B-band 2 is PB2, an intersection point of the principal light ray for the G-band is PG, and an intersection point of the principal light ray for the R-band is PR.

Here, VCAMB1=−1.35% indicates that a position of the intersection point PB1 is nearer to an optical axis than a position of the intersection point PG, and a distance between the intersection point PB1 and the intersection point PG is 1.35% of the maximum image height. Moreover, VCAMB2=−2.6% indicates that a position of the intersection point PB2 is nearer to the optical axis than the position of the intersection point PG, and a distance between the intersection point PB2 and the intersection point PG is 2.6% of the maximum image height. Furthermore, VCAMR=+0.81% indicates that a position of the intersection point PR is nearer to the optical axis than the position of the intersection point PG, and a distance between the intersection point PR and the intersection point PG is 0.81% of the maximum image height.

In an optical system in which the lateral chromatic aberration occurs, a position of an intersection point of a principal light ray and an image plane differs for each band. A difference in the position of the intersection point indicates a shift in position of an optical image occurring in a radial direction.

Correction at the time of white light observation will be described below. In the white light observation, the B-band 1, the G-band, and the R-band are used, and the B-band 2 is not used. Therefore, the representative wavelengths are 460 nm, 540 nm, and 620 nm, and the reference wavelength is 540 nm.

Acquisition of an image in the white light observation is carried out for each of the R-band, the G-band, and the B-band 1. An acquired image for each band is stored in each of differing frame memories.

In electrical correction of the lateral chromatic aberration, correction of the image for the B-band 1 and the image for the R-band is carried out.

The maximum image height of an optical image of the B-band 1 is 1.35% smaller than the maximum image height of an optical image of the G-band. Therefore, correction magnification becomes 1/(1−0.0135)=1.014. The image of the B-band 1 is read from the frame memory of the B-band 1. The image that is read is subjected to 1.014 times electronic enlargement. By doing so, it is possible to make the maximum image height of the image of the B-band 1 coincide with the maximum image height of the image of the G-band.

The maximum image height of an optical image of the R-band is 0.81% larger than the maximum image height of an optical image of the G-band. Therefore, correction magnification becomes 1/(1+0.0081)=0.992. The image of the R-band is read from the frame memory of the R-band. The image that is read is subjected to 0.992 times electronic enlargement. By doing so, it is possible to make the maximum image height of the image of the R-band coincide with the maximum image height of the image of the G-band.

By superimposing the image of the R-band after the electronic enlargement, the image of the G-band, and the image of the B-band 1 after the electronic enlargement, it is possible to achieve a white-light observation image in which the lateral chromatic aberration has been corrected.

Next, correction at the time of the narrow-band light observation will be described below. In the narrow-band light observation, the B-band 2 and the G-band are used, and the B-band 1 and the R-band are not used. Therefore, the representative wavelengths are 415 nm and 540 nm, and the reference wavelength is 540 nm.

Acquisition of an image in the narrow-band light observation is carried out for the G-band and the B-band 2. An acquired image for each band is stored in each of differing frame memories. In the frame memory, a shift in a position of an optical image is stored as a shift in ordinates.

In electrical correction of the lateral chromatic aberration, correction of an image for the B-band 2 is carried out.

The maximum image height of an optical image of the B-band 2 is 2.6% smaller than the maximum image height of an optical image of the G-band. Therefore, the correction magnification becomes 1/(1−0.026)=1.027. The image of the B-band 2 is read from the frame memory of the B-band 2. The image that is read is subjected to 1.027 times electronic enlargement. By doing so, it is possible to make the maximum image height of the image of the B-band 2 coincide with the maximum image height of the image of the G-band.

By superimposing the image of the G-band and the image of the B-band 2 after electronic enlargement, it is possible to achieve a narrow-band light observation image in which the lateral chromatic aberration has been corrected.

The correction methods described above are methods for carrying out correction only by an amount of the lateral chromatic aberration of the representative wavelength for each band. In these methods, the number of representative wavelengths for each band is one. Therefore, these methods are simple correction methods.

The objective optical system of the present embodiment is an optical system in which the lateral chromatic aberration occurs almost linearly with respect to the image height, and an optical system in which the chromatic aberration evaluation value is high. In such optical system, even a simple correction method is effective.

For improving correction accuracy, there is a method of making the number of representative wavelengths for each band in plurality. In this method, a plurality of representative wavelengths is set in a certain band, and weighting of these wavelengths is carried out on the basis of a spectral sensitivity of an imager and a spectral transmittance of an optical system. The lateral chromatic aberration of the plurality of representative wavelengths is calculated, and a weighted average by weighting is calculated, and is let to be an amount of lateral chromatic aberration for that band. Correction is carried out on the basis of the amount of the lateral chromatic aberration calculated.

Moreover, there is a method for calculating a barycentric position from the point spread function of the representative wavelengths for each band. The method of making the number of the representative wavelengths in plurality and the method of calculating a barycenter from the point spread function may be combined.

In both the methods, it is preferable to determine the correction magnification of the lateral chromatic aberration on the basis of design data of the objective optical system. The correction magnification of the lateral chromatic aberration is stored as magnification correction data in a memory of an endoscope.

In a case in which the amount of lateral chromatic aberration is almost linear with respect to the image height, it is possible to carry out a linear lateral chromatic aberration correction. Merits of the linear correction include a fact that an amount of correction data is extremely small. In the white light observation, it is preferable to hold either a value of an optical image magnification for three bands or a value of a reciprocal of the optical image magnification for three bands. The reciprocal of the optical image magnification is nothing but the correction magnification.

In a case in which the value of the lateral chromatic aberration is nonlinear with respect to the image height, a nonlinear lateral chromatic aberration correction has to be carried out. In the nonlinear correction, for accelerating a processing speed, it is necessary to avoid a nonlinear operation at the time of correction processing. For this, the image height from zero to the maximum image height is subjected to multiple division, and a so-called lookup table having an array structure is to be prepared in advance. Data is to be simply read from the array at the time of correction processing, and the nonlinear operation is avoided. Consequently, an amount of correction data becomes extremely large as compared to an amount of correction data in the linear correction.

In an endoscope, apart from the white light observation, various observation methods are used. In these observation methods, electrical correction of the lateral chromatic aberration is carried out according to the requirement. Therefore, correction data becomes necessary for each observation method. Accordingly, an amount of correction data is proportional to the number of observation methods.

Since the number of brands varies according to the observation method, the amount of the correction data varies according to the observation method. The number of bands to be used in one observation is three at the most. Even when the number of bands becomes severalfold according to the number of observation methods, the amount of correction data being small originally in the linear correction, the total amount of the correction data is significantly smaller as compared to the total amount of correction data in the nonlinear correction.

For correcting electrically the lateral chromatic aberration in the endoscope of the present embodiment, it is necessary to create the correction data (magnification correction data) on the basis of the design data of the objective optical system, and to carry out the image processing on the basis of the correction data.

Figure 13:
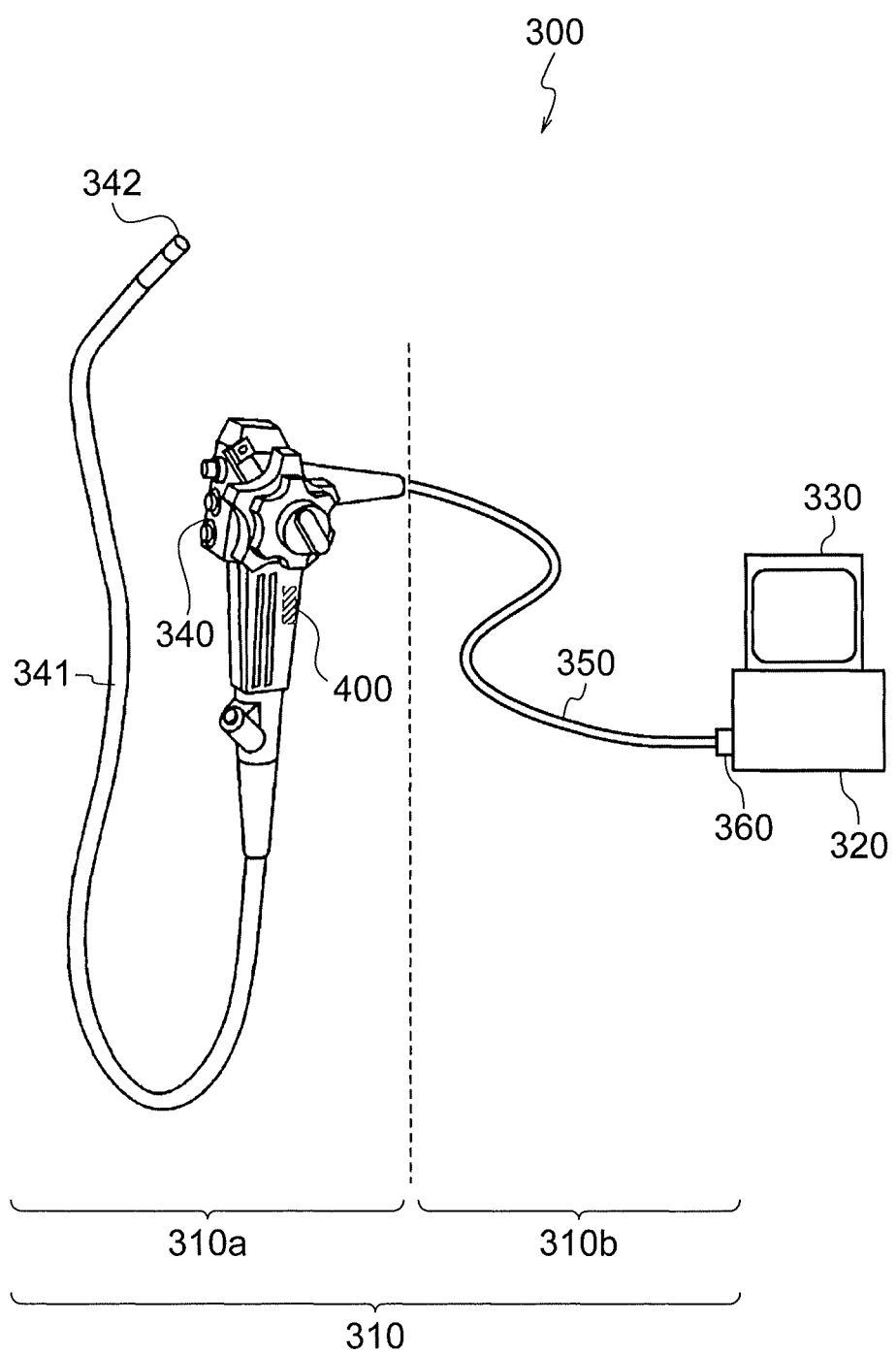
FIG. 13 is a diagram showing a schematic arrangement of an endoscope system.

FIG. 12 shows a schematic arrangement of an endoscope system. In FIG. 13, for explaining an arrangement of the endoscope, only a portion of the endoscope is drawn largely.

The endoscope system 300 includes an endoscope 310 and an image processor 320. The endoscope 310 includes a scope section 310a and a connecting cord section 310b. Moreover, a display unit 330 is connected to the image processor 320.

The scope section 310a is mainly divided into an operating portion 340 and an inserting portion 341. The inserting portion 341 is long and slender, and can be inserted into a body cavity of a patient. Moreover, the inserting portion 341 is formed of a flexible member. An observer can carry out various operations by an angle knob that is provided to the operating portion 340.

Moreover, the connecting cord section 310b is extended from the operating portion 340. The connecting cord section 301b includes a universal cord 350. The universal cord 350 is connected to the image processor 320 via a connector 360.

The universal cord 350 is used for transceiving of various types of signals. Various types of signals include signals such as a power-supply voltage signal and a CCD (charge coupled device) driving signal. These signals are transmitted from a power supply unit and a video processor to the scope section 310a. Moreover, various types of signals include a video signal. This signal is transmitted from the scope section 310a to the video processor.

Peripheral equipment such as a VTR (video tape recorder) deck and a video printer can be connected to the video processor inside the image processor 320. The video processor carries out signal processing on a video signal from the scope section 310a. On the basis of the video signal, an endoscope image is displayed on a display screen of the display unit 330.

An image pickup unit is disposed at a distal end portion 342 of the insertion portion 341. An objective optical system such as the objective optical system of the example 1 is mounted in the image pickup unit.

In the description made above, the video processor is disposed inside the image processor 320. However, the image processor 320 itself may be a video processor. In the following description, a flow of image processing in the endoscope system 300 will be described by using the video processor.

As mentioned above, the objective optical system is mounted in the image pickup unit. The magnification correction data is to be obtained in advance on the basis of the optical design data of the objective optical system. The magnification correction data is data for correcting the lateral chromatic aberration electrically.

At the time of manufacturing the endoscope 310, the magnification correction data is written in the memory 400 in the endoscope 310. As the memory 400, it is possible to use a memory such as a non-volatile memory.

When the endoscope 310 is connected, the video processor reads the magnification correction data that was stored in the non-volatile memory. The magnification correction data that has been read is data in which the lateral chromatic aberration of objective optical system of the endoscope 310 connected is reflected.

Image acquisition using the endoscope 310 is carried out. An acquired image is stored in a frame memory inside the video processor.

The video processor, on the basis of the magnification correction data, carries out the linear correction of the acquired image, for each band.

In the description made above, the endoscope and the magnification correction data correspond one-to-one. However, when the same objective optical system is mounted in an endoscope A and an endoscope B, the same magnification correction data is to be stored in the endoscope A and the endoscope B.

By storing the correction data which depends on the objective optical system in the endoscope, it is possible to optimize an image for each endoscope that is connected. For instance, desirable images differ for a bronchial endoscope and a renal ureteroscope. Even in a case in which the bronchial endoscope and the renal ureteroscope are connected to the same video processor, the magnification correction data corresponding to each endoscope is stored in the endoscope. Accordingly, it is possible to carryout the most suitable image processing for images of each endoscope.

Moreover, on the video processor side, it is preferable to carry out correction processing on the basis of the magnification correction data that was read, and it is not necessary to identify the model of the endoscope connected. Furthermore, even in a case in which an endoscope having a new objective optical system is developed, by holding the magnification correction data in the endoscope, a change on the video processor side becomes unnecessary.

Moreover, by making the correction of the lateral chromatic aberration in the objective optical system such that the amount of lateral chromatic aberration becomes linear with respect to the image height, it is possible to carry out linear correction in the electrical correction. When such an arrangement is made, as it is possible to reduce the amount of correction data by the linear correction, there is no load exerted to the capacity of the non-volatile memory in the endoscope.

In the electrical correction, image enlargement and image reduction are carried out. In a case in which the correction magnification in image enlargement and image reduction is a non-integer multiple, degradation of image to some extent cannot be avoided. In case of observing an image on a monitor, to reduce an effect of image degradation, it is desirable to make a band in which the weighting for a brightness signal displayed on the monitor is high, the reference band.

As no image enlargement and image reduction is carried out in the reference band, no degradation of image occurs in the reference band. As mentioned above, in the reference band, the weighting for the brightness signal being high, a visibility is higher as compared to the other bands. Therefore, even when the degradation of image quality occurs in the other band in which the weighting for the brightness signal is low, as a whole, it is possible to reduce the effect of degradation of image quality. In the G-band, the weighting for the brightness signal is high. Therefore, in the white light observation, it is preferable to make the G-band the reference band.

Depending on the lateral chromatic aberration, sometimes there exists another band for which the image magnification is larger than the image magnification for the reference band. In such case, the electrical correction of another band leads to reduction of image. In the objective optical system of the present embodiment, in the white light observation, in a case in which the G-band is made the reference band, the image magnification for the R-band is larger than the image magnification for the G-band. Therefore, the electrical correction of an image of the R-band becomes a correction in a direction of reducing the image. In this case, it is necessary to use information of a light receiving element positioned at an outer side of the maximum image height (hereinafter, referred to as 'outer-side light receiving element').

As mentioned above, in the image pickup apparatus, microminiaturization has been progressing. In a microminiaturized imager, the number of pixels being about less than 100,000, the number of outer-side light receiving elements is limited. When the number of outer-side light receiving elements is small, the reduction of image becomes difficult. For such reason, in the electrical correction, it is preferable not to carry out reduction of image.

By selecting the reference band, it is possible to make an arrangement not to use information of the outer-side light receiving element. It is preferable to make a band for which the image magnification is the largest among the bands, the reference band. By doing so, in the electrical correction, enlargement of all images is carried out.

In a wavelength region of visible light, the maximum image height becomes the largest in a band on the long-wavelength side. Therefore, in the electrical correction at the time of white light observation, the reference band may be changed from the G-band to the R-band.

Moreover, in a band for which the reduction of image is necessary in the electrical correction, without carrying out the reduction of image presumably, the electric correction may be carried out only for a band for which the enlargement of image is necessary in the electrical correction.

Numerical data for each example described above is shown below. In surface data, r denotes a radius of curvature of each surface, d denotes a thickness or an air-space of each optical member, nd denotes a refractive index for a d-line of each optical member, vd denotes Abbe number for the d-line for each optical member, a stop F denotes a flare stop, and a stop A denotes an aperture stop.

In various data, f denotes a focal length of the overall objective optical system, FNO denotes an F-number, DO denotes an object distance, IH denotes the maximum image height, co denotes a half angle of view, and Lt denotes an overall length of the optical system. Moreover, the unit of r, d, f, DO, IH, and Lt is mm. The unit of ω is ° (degrees).

A definition formula of an aspheric surface used for the numerical data of each example described above is shown below. The definition formula below is an expression indicating an axisymmetric aspheric surface in an S-Z cross-section. In this definition formula, as local coordinates of a plane, an optical axis direction is a Z-axis, and an axis perpendicular to the Z-axis is an S-axis. Moreover, in the following definition formula, no other than fourth order aspherical coefficient is used. This is because it is a simplified indication restricted to an aspherical coefficient of an order used in each example.

$$Z(S) = \frac{S^2/R}{1 + \sqrt{(1-(1+K) \times S^2/R^2)}} + AC_4 \times S^4$$

where,
S denotes a distance from the Z-axis,
Z(S) denotes a Z coordinate which is obtained as a function of S,
R denotes a radius of curvature at a center,
K denotes a conical coefficient, and
$AC_4$ denotes a fourth order aspherical coefficient.

Example 1

| Unit mm Surface data Surface no. | r | d | nd | vd |
|---|---|---|---|---|
| 1 | ∞ | 0.20 | 1.76820 | 71.79 |
| 2 | 0.300 | 0.10 | | |
| 3 (Stop F) | ∞ | 0.03 | | |
| 4 | ∞ | 0.30 | 1.52100 | 65.13 |
| 5 | ∞ | 0.01 | | |
| 6 (Stop A) | ∞ | 0.00 | | |
| 7 | ∞ | 0.45 | 1.67790 | 54.89 |
| 8* | −0.2718 | 0.279 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
8th surface
k = −0.434
A4 = 0

| Various data | |
|---|---|
| f | 0.263 |
| FNO. | 3.529 |
| D0 | 20 |
| IH | 0.242 |
| 2ω | 116.8 |
| Lt | 1.969 |

Example 2

| Unit mm Surface data Surface no. | r | d | nd | vd |
|---|---|---|---|---|
| 1 | ∞ | 0.20 | 1.76820 | 71.79 |
| 2 | 0.300 | 0.10 | | |
| 3 (Stop F) | ∞ | 0.03 | | |
| 4 | ∞ | 0.30 | 1.52100 | 65.13 |
| 5 | ∞ | 0.01 | | |
| 6 (Stop A) | ∞ | 0.00 | | |
| 7 | ∞ | 0.43 | 1.76450 | 49.09 |
| 8* | −0.3006 | 0.2684 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
8th surface
k = −0.3877
A4 = 0

| Various data | |
|---|---|
| f | 0.266 |
| FNO. | 3.562 |
| D0 | 20 |
| IH | 0.242 |
| 2ω | 116.8 |
| Lt | 1.938 |

Example 3

| Unit mm Surface data Surface no. | r | d | nd | vd |
|---|---|---|---|---|
| 1 | ∞ | 0.20 | 1.76820 | 71.79 |
| 2 | 0.300 | 0.10 | | |
| 3 (Stop F) | ∞ | 0.03 | | |
| 4 | ∞ | 0.30 | 1.52100 | 65.13 |
| 5 | ∞ | 0.01 | | |
| 6 (Stop A) | ∞ | 0.00 | | |
| 7 | ∞ | 0.46 | 1.65160 | 58.55 |
| 8* | −0.2634 | 0.2832 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
8th surface
k = −0.4569
A4 = 0

| Various data | |
|---|---|
| f | 0.262 |
| FNO. | 3.514 |
| D0 | 20 |
| IH | 0.242 |
| 2ω | 116.8 |
| Lt | 1.983 |

Example 4

Unit mm
Surface data

| Surface no. | r | d | nd | vd |
|---|---|---|---|---|
| 1 | ∞ | 0.20 | 1.88300 | 40.76 |
| 2 | 0.350 | 0.10 | | |
| 3 | ∞ | 0.03 | | |
| (Stop F) | | | | |
| 4 | ∞ | 0.30 | 1.52100 | 65.13 |
| 5 | ∞ | 0.01 | | |
| 6 | ∞ | 0.00 | | |
| (Stop A) | | | | |
| 7 | ∞ | 0.45 | 1.67790 | 54.89 |
| 8* | −0.2723 | 0.2782 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
8th surface
k = −0.442
A4 = 0

Various data
f        0.265
FNO.     3.529
D0       20
IH       0.242
2ω       116.8
Lt       1.968

Example 5

Unit mm
Surface data

| Surface no. | r | d | nd | vd |
|---|---|---|---|---|
| 1 | ∞ | 0.20 | 1.76820 | 71.79 |
| 2 | 0.300 | 0.10 | | |
| 3 | ∞ | 0.03 | | |
| (Stop F) | | | | |
| 4 | ∞ | 0.30 | 1.52100 | 65.13 |
| 5 | ∞ | 0.01 | | |
| 6 | ∞ | 0.02 | | |
| (Stop A) | | | | |
| 7 | 0.7246 | 0.4 | 1.67790 | 54.89 |
| 8* | −0.3096 | 0.1563 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
8th surface
k = −0.9145
A4 = 0

Various data
f        0.261
FNO.     3.508
D0       20
IH       0.242
2ω       116.8
Lt       1.816

Example 6

Unit mm
Surface data

| Surface no. | r | d | nd | vd |
|---|---|---|---|---|
| 1 | ∞ | 0.20 | 1.76820 | 71.79 |
| 2 | 0.300 | 0.10 | | |
| 3 | ∞ | 0.03 | | |
| (Stop F) | | | | |
| 4 | ∞ | 0.30 | 1.52100 | 65.13 |
| 5 | ∞ | 0.01 | | |
| 6 | ∞ | 0.02 | | |
| (Stop A) | | | | |
| 7* | 0.7186 | 0.4 | 1.67790 | 54.89 |
| 8* | −0.3103 | 0.1558 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
7th surface
k = −26.3142
A4 = 0
8th surface
k = −0.9003
A4 = 0

Various data
f        0.262
FNO.     3.511
D0       20
IH       0.242
2ω       116.8
Lt       1.816

Example 7

Unit mm
Surface data

| Surface no. | r | d | nd | vd |
|---|---|---|---|---|
| 1 | ∞ | 0.20 | 1.76820 | 71.79 |
| 2 | 0.300 | 0.10 | | |
| 3 | ∞ | 0.03 | | |
| (Stop F) | | | | |
| 4 | ∞ | 0.30 | 1.52100 | 65.13 |
| 5 | ∞ | 0.01 | | |
| 6 | ∞ | 0.02 | | |
| (Stop A) | | | | |
| 7* | ∞ | 0.43 | 1.67790 | 54.89 |
| 8* | −0.2743 | 0.2854 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
7th surface
k = 0
A4 = −20.751
8th surface
k = −0.4421
A4 = 0

Various data
f        0.264
FNO.     3.533
D0       20
IH       0.242
2ω       116.8
Lt       1.975

Example 8

Unit mm
Surface data

| Surface no. | r | d | nd | vd |
|---|---|---|---|---|
| 1 | ∞ | 0.20 | 1.76820 | 71.79 |
| 2 | 0.300 | 0.10 | | |
| 3 | ∞ | 0.03 | | |
| (Stop F) | | | | |
| 4 | ∞ | 0.45 | 1.52100 | 65.13 |
| 5 | ∞ | 0.01 | | |
| 6 | ∞ | 0.02 | | |
| (Stop A) | | | | |
| 7 | 0.7634 | 0.36 | 1.67790 | 54.89 |
| 8* | −0.4174 | 0.3616 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
8th surface
k = −1.3326
A4 = 0

Various data
| | |
|---|---|
| f | 0.322 |
| FNO. | 4.092 |
| D0 | 6.5 |
| IH | 0.242 |
| 2ω | 90 |
| Lt | 2.132 |

Example 9

Unit mm
Surface data

| Surface no. | r | d | nd | vd |
|---|---|---|---|---|
| 1 | ∞ | 0.18 | 1.76820 | 71.79 |
| 2 | 0.25 | 0.09 | | |
| 3 | ∞ | 0.01 | | |
| (Stop F) | | | | |
| 4 | ∞ | 0.25 | 1.52100 | 65.13 |
| 5 | ∞ | 0.01 | | |
| 6 | ∞ | 0.02 | | |
| (Stop A) | | | | |
| 7 | 0.6717 | 0.39 | 1.67790 | 54.89 |
| 8* | −0.2509 | 0.1 | | |
| 9 | ∞ | 0.25 | 1.51633 | 64.14 |
| 10 | ∞ | 0.30 | 1.51633 | 64.14 |
| 11 (Image plane) | ∞ | | | |

Aspherical surface data
8th surface
k = −0.8295
A4 = 0

Various data
| | |
|---|---|
| f | 0.212 |
| FNO. | 3.279 |
| D0 | 20 |
| IH | 0.198 |
| 2ω | 116.8 |
| Lt | 1.6 |

Example 10

Unit mm
Surface data

| Surface no. | r | d | nd | vd |
|---|---|---|---|---|
| 1 | ∞ | 0.18 | 1.76820 | 71.79 |
| 2 | 0.25 | 0.09 | | |
| 3 | ∞ | 0.01 | | |
| (Stop F) | | | | |
| 4 | ∞ | 0.25 | 1.52100 | 65.13 |
| 5 | ∞ | 0.01 | | |
| 6 | ∞ | 0.02 | | |
| (Stop A) | | | | |
| 7 | 0.633 | 0.37 | 1.67790 | 54.89 |
| 8* | −0.3005 | 0.2054 | | |
| 9 | ∞ | 0.30 | 1.51633 | 64.14 |
| 10 | ∞ | 0.30 | 1.51633 | 64.14 |
| 11 (Image plane) | ∞ | | | |

Aspherical surface data
8th surface
k = −0.8984
A4 = 0

Various data
| | |
|---|---|
| f | 0.265 |
| FNO. | 3.789 |
| D0 | 20 |
| IH | 0.198 |
| 2ω | 90 |
| Lt | 1.685 |

Next, the values of conditional expressions (1) to (5) in each example are shown below.

| Conditional Expression | Example 1 | Example 2 | Example 3 |
|---|---|---|---|
| (1) LL1is/LsL2i | 0.749 | 0.784 | 0.733 |
| (2) (LL1is/RL1i) × (LsL2i/RL2i) | −1.861 | −1.608 | −1.963 |
| (3) fL2$^2$/(f × fL1) | −1.564 | −1.485 | −1.593 |
| (4) (nd1−1.63) × (vd1−31) | 5.64 | 5.64 | 5.64 |
| (5) (nd2−1.45) × (vd2−31) | 5.44 | 5.69 | 5.55 |

| Conditional Expression | Example 4 | Example 5 | Example 6 |
|---|---|---|---|
| (1) LL1is/LsL2i | 0.749 | 0.803 | 0.803 |
| (2) (LL1is/RL1i) × (LsL2i/RL2i) | −1.592 | −1.525 | −1.522 |
| (3) fL2$^2$/(f × fL1) | −1.54 | −1.408 | −1.402 |
| (4) (nd1−1.63) × (vd1−31) | 2.47 | 5.64 | 5.64 |
| (5) (nd2−1.45) × (vd2−31) | 5.44 | 5.44 | 5.44 |

| Conditional Expression | Example 7 | Example 8 | Example 9 |
|---|---|---|---|
| (1) LL1is/LsL2i | 0.749 | 1.147 | 0.669 |
| (2) (LL1is/RL1i) × (LsL2i/RL2i) | −1.844 | −1.323 | −1.793 |
| (3) fL2$^2$/(f × fL1) | −1.589 | −1.637 | −1.533 |
| (4) (nd1−1.63) × (vd1−31) | 5.64 | 5.64 | 5.64 |
| (5) (nd2−1.45) × (vd2−31) | 5.44 | 5.44 | 5.44 |

-continued

| Conditional Expression | Example 10 |
|---|---|
| (1)LL1is/LsL2i | 0.704 |
| (2)(LL1is/RL2i) × (LsL2i/RL2i) | −1.424 |
| (3)fL2²/(f × fL1) | −1.488 |
| (4)(nd1-1.63) × (vd1-31) | 5.64 |
| (5)(nd2-1.45) × (vd2-31) | 5.44 |

According to the present embodiment, it is possible to provide an objective optical system which is suitable for microminiaturized mounting, and which has a favorable imaging performance with the improved longitudinal chromatic aberration, and an endoscope, and an endoscope system.

As it has been described heretofore, the present disclosure is useful for an objective optical system which is suitable for microminiaturized mounting, and which has a favorable imaging performance with the improved longitudinal chromatic aberration, and an endoscope and an endoscope system.

What is claimed is:

1. An objective optical system, consisting of in order from an object side to an image side:
    a first lens having a negative refractive power;
    an aperture stop; and
    a second lens having a positive refractive power, wherein
    an image-side surface of the first lens is concave toward the image side,
    an image-side surface of the second lens is convex toward the image side, and
    following conditional expressions (1), (2), (3), (4), (5), (6), and (7) are satisfied:

$$0.6 < LL1is/LsL2i < 1.25 \quad (1)$$

$$-3 < (LL1is/RL1i) \times (LsL2i/RL2i) < -1.25 \quad (2)$$

$$-2 < fL2^2/(f \times fL1) < -1.35 \quad (3)$$

$$2 < (nd1-1.63) \times (vd1-31) \quad (4)$$

$$5 < (n2-1.45) \times (vd2-31) \quad (5)$$

$$1.63 < nd1, \text{ and, } 31 < vd1 \quad (6)$$

$$1.45 < nd2, \text{ and, } 31 < vd2 \quad (7)$$

where,
LL1is denotes an air conversion length from the image-side surface of the first lens up to the aperture stop,
LsL2i denotes a distance from the aperture stop up to the image-side surface of the second lens,
RL1i denotes a radius of curvature of the image-side surface of the first lens,
RL2i denotes a radius of curvature of the image-side surface of the second lens,
fL1 denotes a focal length of the first lens,
fL2 denotes a focal length of the second lens,
f denotes a focal length of the objective optical system,
nd1 denotes a refractive index for a d-line of the first lens,
vd1 denotes Abbe number for the first lens,
nd2 denotes a refractive index for the d-line of the second lens, and
vd2 denotes Abbe number for the second lens.

2. The objective optical system according to claim 1, wherein
    the image-side surface of the second lens is an aspheric surface, and
    a curvature of the aspheric surface is smaller at a periphery than at a center.

3. The objective optical system according to claim 2, wherein the second lens is a planoconvex lens.

4. The objective optical system according to claim 2, wherein
    the second lens is a biconvex lens, and
    an object-side surface of the second lens is a surface which is convex toward the object side.

5. The objective optical system according to claim 2, wherein
    the second lens is a biconvex lens,
    an object-side surface of the second lens is a surface which is convex toward the object side,
    the object-side surface of the second lens is an aspheric surface, and
    a curvature of the aspheric surface of the object-side surface is smaller at a periphery than at a center.

6. The objective optical system according to claim 2, wherein
    the second lens is a convex meniscus lens, and
    an object-side surface of the second lens is an aspheric surface having a negative refractive power at a periphery.

7. An endoscope, comprising:
    an objective optical system according to claim 1; and
    an image sensor which captures an image formed by the objective optical system.

8. The endoscope according to claim 7, wherein
    the image-side surface of the second lens is an aspheric surface, and
    a curvature of the aspheric surface is smaller at a periphery than at a center.

9. The endoscope according to claim 8, wherein the second lens is a planoconvex lens.

10. The endoscope according to claim 8, wherein
    the second lens is a biconvex lens, and
    an object-side surface of the second lens is a surface which is convex toward the object side.

11. The endoscope according to claim 8, wherein
    the second lens is a biconvex lens,
    an object-side surface of the second lens is a surface which is convex toward the object side,
    the object-side surface of the second lens is an aspheric surface, and
    a curvature of the aspheric surface of the object-side surface is smaller at a periphery than at a center.

12. The endoscope according to claim 8, wherein
    the second lens is a convex meniscus lens, and
    an object-side surface of the second lens is an aspheric surface having a negative refractive power at a periphery.

13. An endoscope system, comprising:
    an endoscope according to claim 7; and
    an image processor, wherein
    the endoscope has a memory which stores data for image correction,
    the data for image correction includes magnification correction data created on the basis of design data of the objective optical system,
    the magnification correction data is data for correcting a lateral chromatic aberration in an image captured by the image sensor, and the image processor corrects the lateral chromatic aberration on the basis of the magnification correction data for at least one of an R-band, a G-band, and a B-band.

14. The endoscope system according to claim 13, wherein the image-side surface of the second lens is an aspheric surface, and
a curvature of the aspheric surface is smaller at a periphery than at a center.

15. The endoscope system according to claim 14, wherein the second lens is a planoconvex lens.

16. The endoscope system according to claim 14, wherein the second lens is a biconvex lens, and
an object-side surface of the second lens is a surface which is convex toward the object side.

17. The endoscope system according to claim 14, wherein the second lens is a biconvex lens,
an object-side surface of the second lens is a surface which is convex toward the object side,
the object-side surface of the second lens is an aspheric surface, and
a curvature of the aspheric surface of the object-side surface is smaller at a periphery than at a center.

18. The endoscope system according to claim 14, wherein the second lens is a convex meniscus lens, and
an object-side surface of the second lens is an aspheric surface having a negative refractive power at a periphery.

* * * * *